(12) United States Patent
Shioya et al.

(10) Patent No.: US 8,642,999 B2
(45) Date of Patent: Feb. 4, 2014

(54) ORGANIC LIGHT-EMITTING DEVICE AND DISPLAY APPARATUS

(75) Inventors: Shunsuke Shioya, Yokohama (JP); Satoru Shiobara, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 687 days.

(21) Appl. No.: 12/598,947

(22) PCT Filed: Sep. 12, 2008

(86) PCT No.: PCT/JP2008/066939
§ 371 (c)(1),
(2), (4) Date: Nov. 5, 2009

(87) PCT Pub. No.: WO2009/038156
PCT Pub. Date: Mar. 26, 2009

(65) Prior Publication Data
US 2010/0133521 A1    Jun. 3, 2010

(30) Foreign Application Priority Data
Sep. 18, 2007  (JP) .................................. 2007-240660

(51) Int. Cl.
*H01L 29/08*    (2006.01)
(52) U.S. Cl.
USPC .......................................................... 257/40
(58) Field of Classification Search
USPC ............. 257/40, E51.032, E51.044; 428/690, 428/917
See application file for complete search history.

(56) References Cited

U.S. PATENT DOCUMENTS

| 6,235,414 | B1 | 5/2001 | Epstein et al. ................. 428/690 |
| 7,057,009 | B2 | 6/2006 | Chen et al. |
| 7,229,702 | B2 * | 6/2007 | Saitoh et al. ................... 428/690 |
| 2003/0039838 | A1 * | 2/2003 | Chen et al. ................. 428/411.1 |
| 2005/0106414 | A1 | 5/2005 | Saitoh et al. |
| 2006/0251886 | A1 | 11/2006 | Müller et al. ................... 428/339 |
| 2007/0114521 | A1 * | 5/2007 | Hayashi et al. .................. 257/40 |
| 2007/0248840 | A1 * | 10/2007 | Lin et al. ........................ 428/690 |
| 2007/0257603 | A1 * | 11/2007 | Suzuki et al. .................. 313/504 |
| 2007/0292717 | A1 | 12/2007 | Watanabe et al. ............. 428/690 |
| 2008/0220289 | A1 * | 9/2008 | Shioya et al. .................. 428/691 |

FOREIGN PATENT DOCUMENTS

| CN | 1568303 A | 1/2005 |
| JP | 2002-508107 | 3/2002 |
| JP | 2002-317033 | 10/2002 |
| JP | 2003-055275 | 2/2003 |
| JP | 2007-504656 | 3/2007 |
| WO | 03/080559 A1 | 10/2003 |

OTHER PUBLICATIONS

Ahn, J.H. et al. "Blue Organic Light Emitting Devices With Improved Color Purity and Efficiency Through Blending of Poly(9,9-Dioctyl-2.7-Fluorene) with an Electron Transporting Material." J. Mater. Chem., vol. 17 (2007): pp. 2996-3001.*

(Continued)

*Primary Examiner* — Yu-Hsi D Sun
*Assistant Examiner* — Christina Sylvia
(74) *Attorney, Agent, or Firm* — Fitzpatrick, Cella, Harper & Scinto

(57) ABSTRACT

Provided is an organic light-emitting device having a high emission efficiency and a long lifetime. The organic light-emitting device (10) includes an anode (2), a cathode (6), and a stack body including at least a light-emitting layer (4) and interposed between the anode (2) and the cathode (6), in which the light-emitting layer (4) includes an oligomer material and a polymer material.

12 Claims, 6 Drawing Sheets

(56) References Cited

OTHER PUBLICATIONS

Oliva, M.M., et al. "Electronic and Molecular Structures of Trigonal Truxene-Core Systems Conjugated to Peripheral Fluorene Branches. Spectroscopic and Theoretical Study." J. Phys. Chem. B, vol. 111 (2007): pp. 4026-4035.*

Janietz, S., et al. "Electrochemical Determination fo the Ionization Potential and Electron Affinity fo Poly(9,9-Dioctylfluorene)." Appl. Phys. Lett., vol. 73 (1998): pp. 2453-2455.*

Feng, G.-L., et al. "Synthesis of Novel Star-Shaped Carbazole-Functionalized Triazatruxenes." Tetra. Lett., vol. 47 (2006): pp. 7089-7092.*

Evans, R.C., et al. "Coordination Complexes Exhibiting Room-Temperature Phosphorescence: Evaluation of their Suitablility as Triplet Emitters in Organic Light Emitting Diodes." Coor. Chem. Rev., vol. 250 (2006): pp. 2093-2126.*

Sean W. Culligan et al., "Strongly Polarized and Efficient Blue Organice Light-Emitting Diodes Using Monodisperse Glassy Nematic Oligo(fluorene)s**," Advanced Materials, vol. 15, No. 14, Jul. 17, pp. 1176-1180.

Alexander L. Kanibolotsky et al., "Synthesis and Properties of Monodisperse Oligofluorene-Functionalized truxenes: Highly Fluorescent Star-Shaped Architectures," J.Am. Chem. Soc., vol. 126, 2004, pp. 13695-13702.

Guo-Liang Feng et al., "Synthesis of novel star-shaped carbazole-functionalized triazatruxenes," Tetrahedron Letters vol. 47, 2006, pp. 7089-7092.

Lai, et al., "Monodisperse Six-Armed Triazatruxenes: Microwave-Enhanced Synthesis and Highly Efficient Pure-Deep-Blue Electroluminescence", Macromolecules, 2006, 39(11), pp. 3707-3709.

Chinese office action issued in counterpart application No. 200880024380.5 dated Mar. 17, 2011 and its English-language translation—10 pages.

European Office Action issued corresponding to application No. 08831368.9 dated Jan. 20, 2012—11 pages.

P. A. Levermore et al., "Deep-blue light emitting triazatruxene core/oligo-fluorene branch dendrimers for electroluminescence and optical gain applications", J. Phys. D: Appl. Phys. vol. 40 (2007), pp. 1896-1901.

C. Jiang et al., "High-Efficiency, Saturated Red-Phosphorescent Polymer Light-Emitting Diodes Based on Conjugated and Non-Conjugated Polymers Doped with an Ir Complex", Adv. Mater, vol. 16, No. 6, Mar. 18, 2004, pp. 537-541.

English translation of Korean Office Action issued in corresponding application No. 10-2011-7024933 on Jan. 31, 2012—4 pages.

* cited by examiner

ORGANIC LIGHT-EMITTING DEVICE AND DISPLAY APPARATUS

TECHNICAL FIELD

The present invention relates to an organic light-emitting device and a display apparatus.

BACKGROUND ART

The electroluminescent device is a self-emission type device and therefore has high visibility, is excellent in display performance, can respond at a high speed, and can be reduced in thickness. Accordingly, the electroluminescent device has been attracting attention as a display device such as a flat panel display.

Of the electroluminescent device, an organic light-emitting device using an organic compound as a light-emitting body has, for example, such characteristics that the device can be driven at a lower voltage than a drive voltage of an inorganic light-emitting device, the area of the device can be easily enlarged, and a desired emission color can easily be obtained by selecting an appropriate coloring matter. Accordingly, the organic light-emitting device has been actively developed as a next-generation display.

Here, as the process of producing an organic light-emitting device using an organic light-emitting body, there are included a process involving producing a low-molecular-weight compound by a dry process such as vacuum evaporation, and a coating film formation process such as a spin coating method, a casting method, and an ink-jet method.

In a case of producing the device by the coating film formation process, the organic light-emitting device produced by the coating film formation process (hereinafter, simply referred to as "coating organic light-emitting device") has, for example, the following merits compared to the organic light-emitting device produced by the dry process:

(1) the device can be produced at low cost;
(2) the device can be increased in area easily; and
(3) the controllability of doping in a slight amount is excellent.

FIG. 9 is a cross-sectional view illustrating a general structure of a coating organic light-emitting device. An organic light-emitting device 110 illustrated in FIG. 9 has an anode 101, a hole injection layer 102, a light-emitting layer 103, an electron injection layer 104, and a cathode 105 formed sequentially on a substrate 100.

In the organic light-emitting device 110 shown in FIG. 9, a mixture of polythiophene and polystyrene sulfonic acid (PEDOT:PSS) is generally used as a constituent material of the hole injection layer 102, and the film is formed by a spin coating method or the like. Here, the mixture PEDOT:PSS is soluble in water and insoluble in an organic solvent. Accordingly, even when the light-emitting layer 103 is formed by dissolving a constituent material of the light-emitting layer 103 in a non-polar solvent and by coating the solution on the PEDOT:PSS film, the PEDOT:PSS film is not eluted. Therefore, the PEDOT:PSS is regarded as a suitable hole injection material for production of a coating organic light-emitting device.

For the formation of the light-emitting layer 103, a polymer compound is mainly used. This is because the polymer compound has high amorphous property and therefore hardly crystallizes as compared to a low-molecular compound. Specific examples of the materials used include polymers such as polyvinyl carbazole (PVK) which is a disconjugated polymer, polyphenylene vinylene (PPV) and polyfluorene (PF) which are n-conjugated polymers, and derivatives thereof. In particular, the n-conjugated polymer is also referred to as "conductive polymer". The polymer material which is a constituent material of the light-emitting layer 103 is formed into a solution, and then formed into a film by a spin coating method, an inkjet method or the like.

Next, the electron injection layer 104 composed of lithium fluoride or the like and a metal electrode which becomes the cathode 105 are sequentially formed on the light-emitting layer 103 by employing a vacuum evaporation method, whereby an organic light-emitting device is completed.

As described above, the coating organic light-emitting device can be produced by a simple process. Accordingly, the device is expected to find use in a wide variety of applications. However, the device involves such a problem to be solved that the device does not have a sufficient lifetime.

Various assumptions have been made about the causes for the fact that the device does not have a sufficient lifetime. One of the causes is considered to be difficulty in molecular weight control or purification of the polymer compound as a constituent material of the light-emitting layer 103.

One possible approach to solving the above problem involves use of an oligomer material the molecular weight control and purification of which can be easily performed as compared to a polymer material and which has higher amorphous property as compared to a low-molecular material. The oligomer material is excellent in purity and coating performance, and in addition, has high degree of freedom of material design, and various units such as a hole-transporting part, an electron-transporting part, and a light-emitting part can be provided at desired parts. Accordingly, the widening of the scope of material design is also included as a merit.

As examples of the application of an oligomer material to an organic light-emitting device, there are included applications disclosed in Advanced Material, S. W. Culligan et al., 2003, 15, No. 14, p 1176; J. Am. CHEM. SOC., A. L. Kanibolotsky et al., 2004, 126, p 13695; and Tetrahedron. Lett., G. L. Feng et al., 2006, 47, p 7089 and Japanese Patent Application Laid-Open No. 2003-055275.

In addition, another cause for the fact that the device does not have sufficient lifetime is considered to be that a space where electric charge is readily accumulated (space charge layer) is generated at an interface between respective layers and degrades the material.

The problem of space charge layer is solved by a well-known conventional technology, that is, by mixing a polymer or a low-molecular compound each having an electron-transporting property or a hole-transporting property in a polymer light-emitting layer to thereby improve the injectability of carriers into the light-emitting layer.

Meanwhile, the oligomer material is easily purified for achieving high purity compared to a polymer material because of having no molecular weight distribution, with the result that the lifetime of the device can be lengthened. However, it is realistic that the oligomer material has a molecular weight of about 10,000 or less from the viewpoint of synthesis of the material. Here, the oligomer material having a molecular weight of about 10,000 or less hardly causes crystallization or aggregation as compared to low-molecular materials and the stability of a film is improved. However, there is a fear of posing problems such as crystallization or aggregation when compared to polymer materials.

On the other hand, there is known a conventional technology for lengthening the lifetime of the organic light-emitting device by improving the carrier injectability as a result of mixing a plurality of materials in a light-emitting layer for the purpose of appropriately adjusting a HOMO level, a LUMO level, an electron mobility, and a hole mobility. In the case of the coating organic light-emitting device, there are known a polymer-polymer mixture type and a polymer-low molecular compound mixture type. However, in the case of the polymer-polymer mixture type, it is necessary to consider the compatibility of the polymer materials with each other, resulting in less choice of the polymers to be mixed. Accordingly, the polymer-polymer mixture type is not generic method. In addition, in the case of the polymer-low molecular compound mixture type, when the amount of the low-molecular material is increased, the low-molecular material will be crystallized or aggregated, resulting in difficulty in uniform mixing with desired amounts.

DISCLOSURE OF THE INVENTION

The present invention has been accomplished in view of the above-mentioned problems, and it is an object of the present invention to provide an organic light-emitting device having a high emission efficiency and a long lifetime. It is another object of the present invention to provide an organic light-emitting device that can be produced by a coating process which is an easy and low cost process.

The organic light-emitting device of the present invention includes an anode, a cathode, a stack body including at least a light-emitting layer and interposed between the anode and the cathode, in which the light-emitting layer includes an oligomer material and a polymer material.

According to the present invention, an organic light-emitting device having a high emission efficiency and a long lifetime can be provided. In addition, according to the present invention, an organic light-emitting device capable of being produced by a coating process which is easy and low cost can be provided.

Further features of the present invention will become apparent from the following description of exemplary embodiments with reference to the attached drawings.

BRIEF DESCRIPTION OF THE DRAWINGS

FIG. 7A is a photograph in a case of Example 1 and FIG. 7B is a photograph in a case of Comparative Example 3.

FIG. 8A is a photograph in the case of Example 1 and FIG. 8B is a photograph in the case of Comparative Example 1.

BEST MODE FOR CARRYING OUT THE INVENTION

Figure 1:
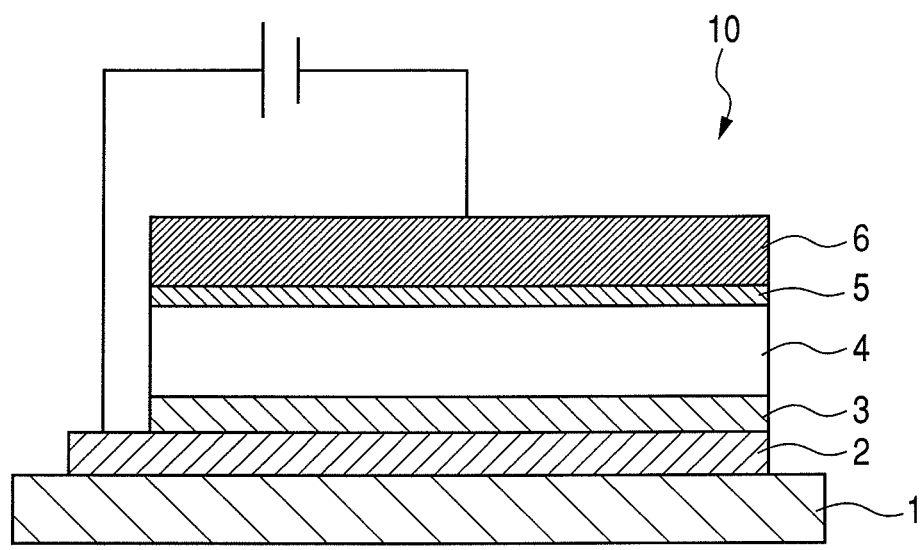
FIG. 1 is a cross-sectional view illustrating an organic light-emitting device according to a first embodiment of the present invention.

Hereinafter, the present invention will be described in detail. However, the present invention is not limited by the following description.

The organic light-emitting device of the present invention is constituted of an anode, a cathode, and a stack body including at least a light-emitting layer and interposed between the anode and the cathode.

Hereinafter, the organic light-emitting device of the present invention will be described in detail with reference to the accompanying drawings.

First, reference numerals used in the figures will be described.

An organic light-emitting device 10 includes a substrate 1, an anode 2, a hole injection layer 3, a light-emitting layer 4, an electron injection layer 5, and a cathode 6. An organic light-emitting device 20 further includes a hole-transporting layer 7 and an electron-transporting layer 8. An organic light-emitting device 30 further includes an electron-blocking layer 9.

A display apparatus 40 includes a scanning signal driver 41, an information signal driver 42, a current supply source 43, and pixel circuits 44 and 50.

A circuit 50 includes a first thin film transistor (TFT) 51, a capacitor ($C_{add}$) 52, and a second thin film transistor (TFT) 53.

A display apparatus 60 includes a substrate 61, a moisture resistant layer 62, a gate electrode 63, a gate insulating film 64, a semiconductor film 65, a drain electrode 66, a source electrode 67, a TFT element 68, an insulating film 69, a contact hole (through-hole) 70, an anode 71, an organic layer 72, a cathode 73, a first protective layer 74, and a second protective layer 75. An organic light-emitting device 110 includes a substrate 100, an anode 101, a hole injection layer 102, a light-emitting layer 103, an electron injection layer 104, and a cathode 105.

FIG. 1 is a cross-sectional view illustrating an organic light-emitting device according to a first embodiment of the present invention. The organic light-emitting device 10 illustrated in FIG. 1 has the anode 2, the hole injection layer 3, the light-emitting layer 4, the electron injection layer 5, and the cathode 6 sequentially provided on the substrate 1.

Figure 2:
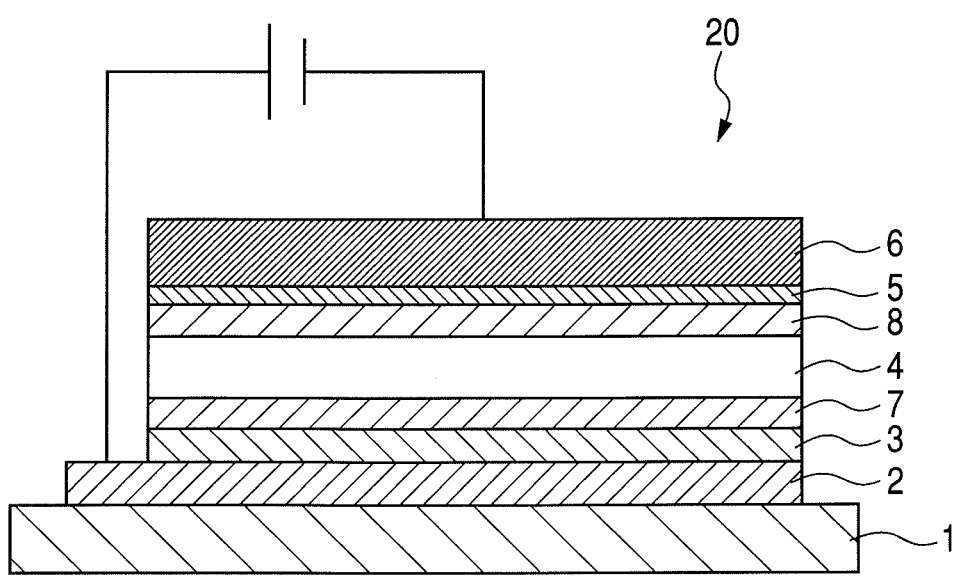
FIG. 2 is a cross-sectional view illustrating an organic light-emitting device according to a second embodiment of the present invention.

FIG. 2 is a cross-sectional view illustrating an organic light-emitting device according to a second embodiment of the present invention. The organic light-emitting device 20 illustrated in FIG. 2 is obtained by providing the hole-transporting layer 7 between the hole injection layer 3 and the light-emitting layer 4 and providing the electron-transporting layer 8 between the light-emitting layer 4 and the electron injection layer 5 in the organic light-emitting device 10 illustrated in FIG. 1. By providing the hole-transporting layer 7 and the electron-transporting layer 8, the injectability of carriers into the light-emitting layer 4 is improved.

Figure 3:
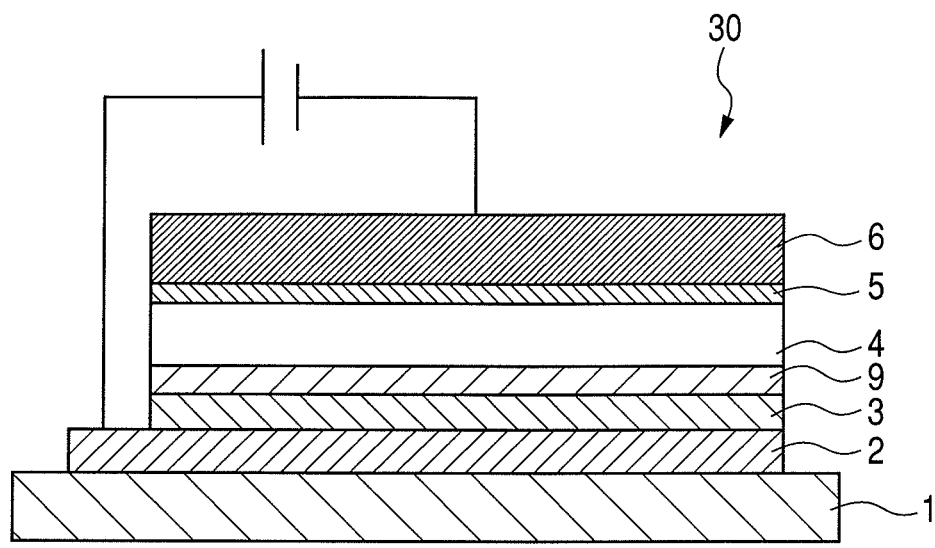
FIG. 3 is a cross-sectional view illustrating an organic light-emitting device according to a third embodiment of the present invention.

FIG. 3 is a cross-sectional view illustrating an organic light-emitting device according to a first embodiment of the present invention. The organic light-emitting device 30 illustrated in FIG. 3 is obtained by providing the electron-blocking layer 9 between the hole injection layer 3 and the light-emitting layer 4 in the organic light-emitting device 10 illustrated in FIG. 1. By providing the electron-blocking layer 9, electrons or excitons are prevented from passing through the light-emitting layer 4 to the anode 2 side. Therefore, the structure of the organic light-emitting device 30 is effective for improving the emission efficiency.

However, the organic light-emitting device of the present invention is not limited to the above embodiments. For example, there can be included an exemplary structure in which only the light-emitting layer 4 is provided between the anode 2 and the cathode 6. In addition, a structure can be included in which a hole-transporting layer or an electron-transporting layer is further provided in the organic light-emitting device 10 shown in FIG. 1. Further, there can be included a structure in which a hole-blocking layer is provided between the light-emitting layer 4 and the electron injection layer 5. There can also be included an exemplary structure in which an electron-blocking layer is provided between the light-emitting layer 4 and the hole injection layer 3 and a hole-blocking layer is provided between the light-emitting layer 4 and the electron injection layer 5.

In the organic light-emitting device of the present invention, the light-emitting layer includes an oligomer material and a polymer material.

The term "oligomer material" herein employed refers to a material having a molecular weight of 1,000 to 10,000 and having no molecular weight distribution. Accordingly, the oligomer material can be highly purified by a purification method such as a column chromatography or a gel permeation chromatography.

The oligomer material is preferably a compound having a fluorene unit. The compound having a fluorene unit is chemically, thermally, and electrochemically stable, and is therefore used as a constituent material of organic light-emitting devices. Therefore, when the oligomer material is a compound having a fluorene unit, a more stable device can be produced, whereby a device having a high efficiency and a long lifetime can be produced.

Hereinafter, examples of the oligomer material used as a constituent material of the organic light-emitting device of the present invention are given, but the present invention is not limited thereto.

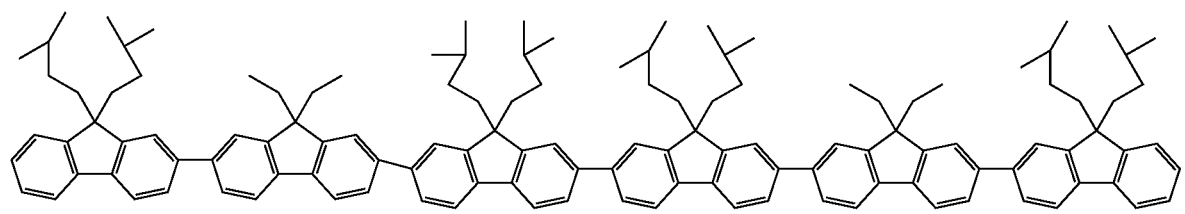

No. 1

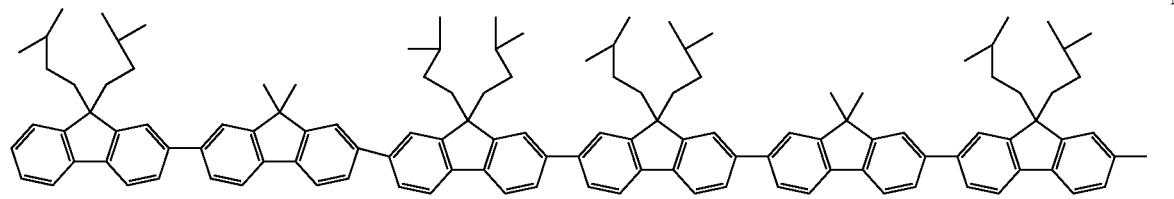

No. 2

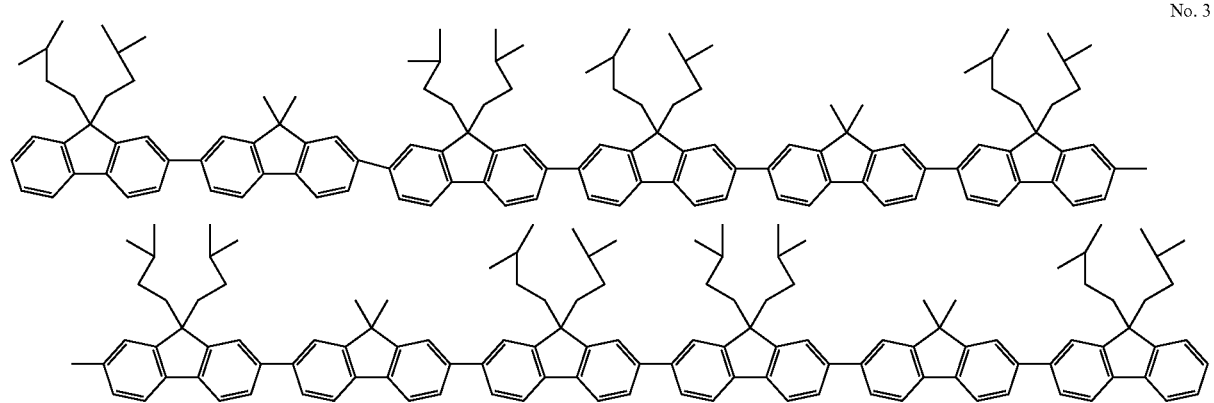

No. 3

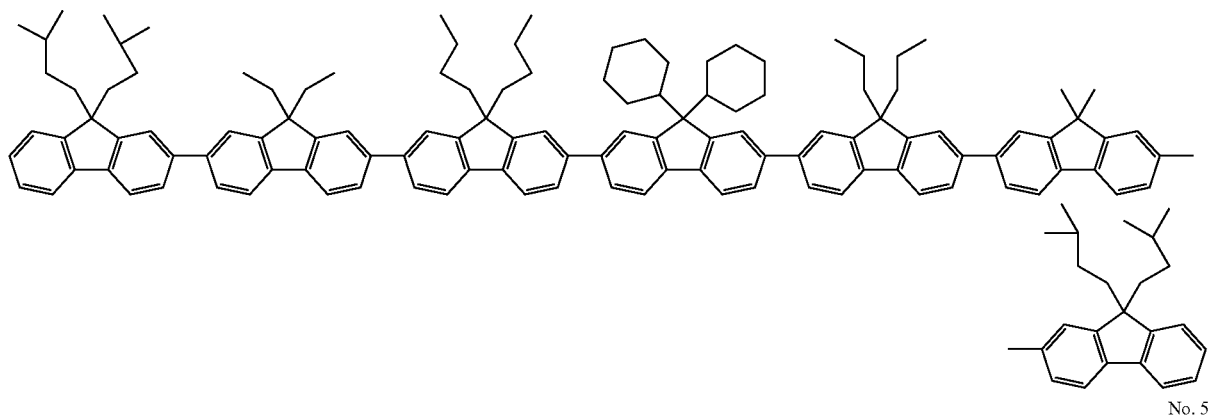
No. 4
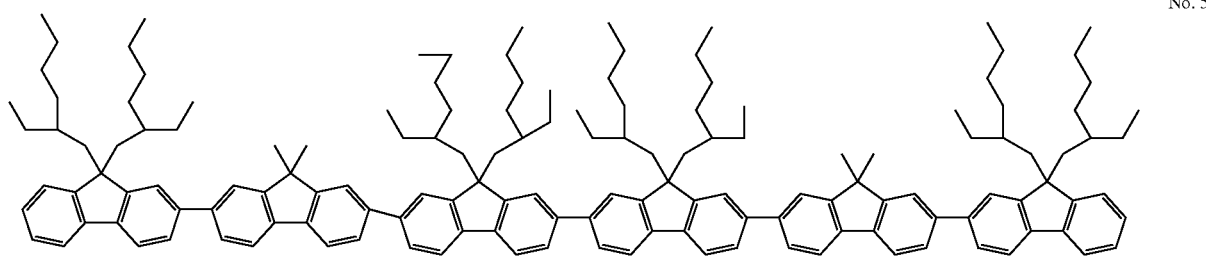
No. 5
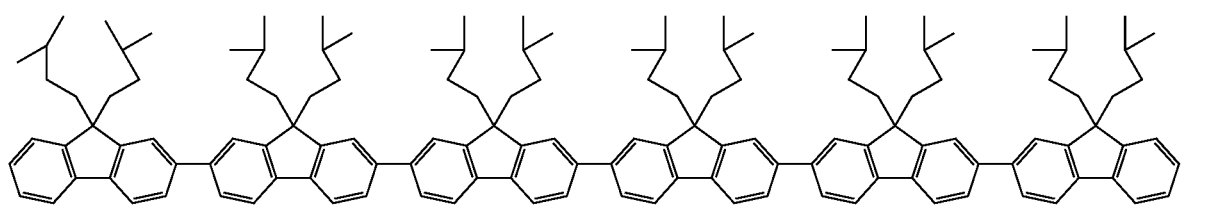
No. 6
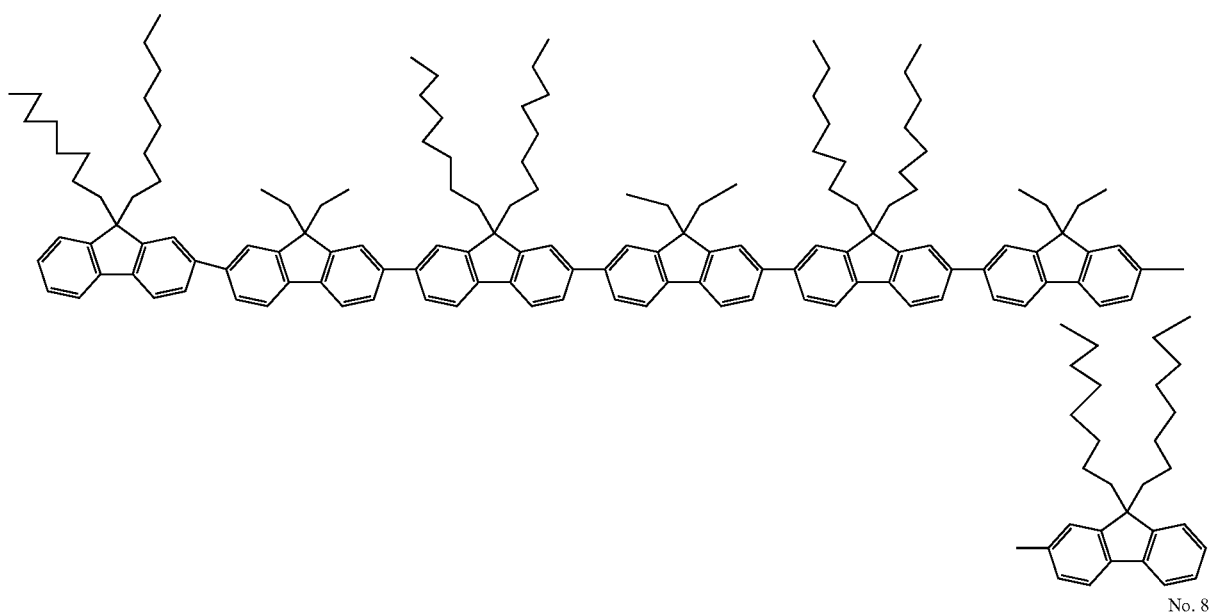
No. 7
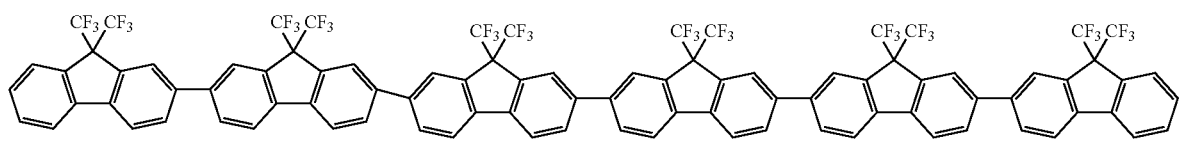
No. 8

-continued
No. 9
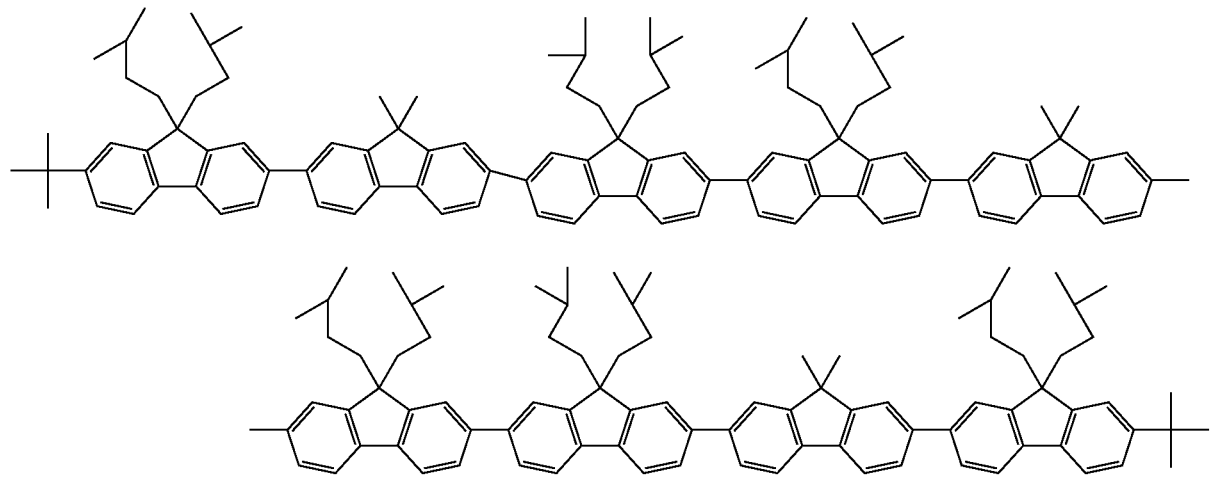
No. 10
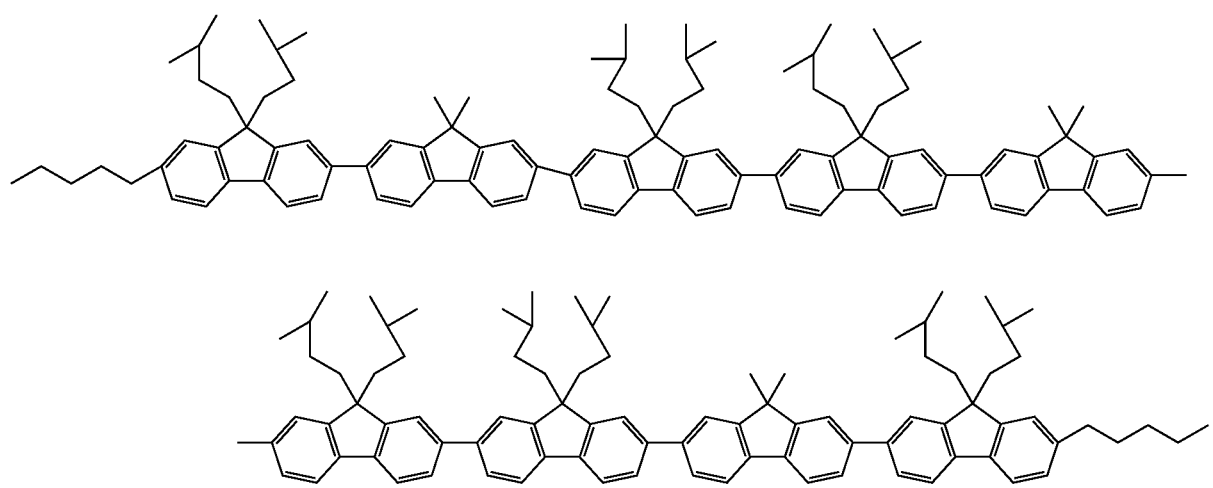
No. 11
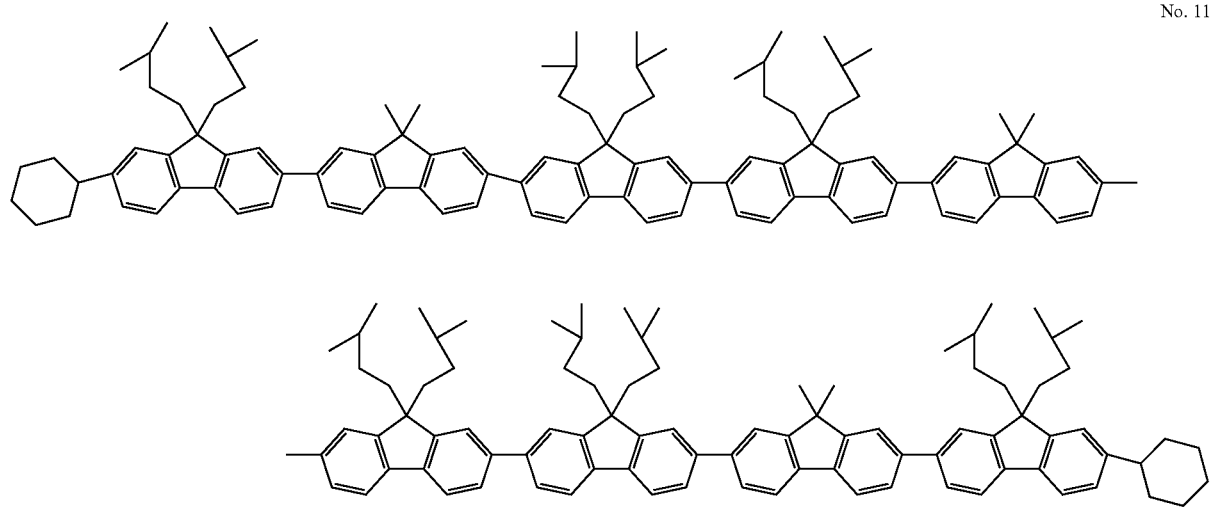

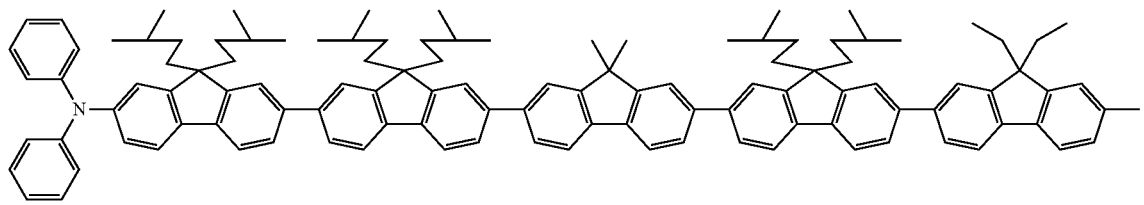
No. 12
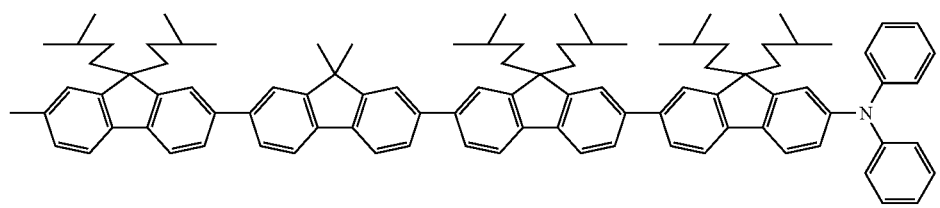
No. 13
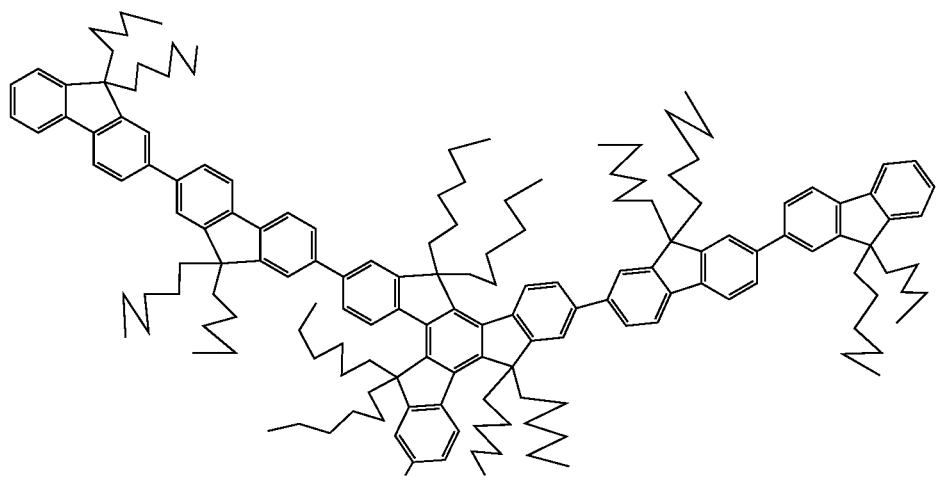
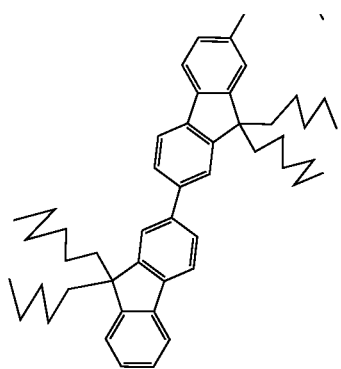

No. 14
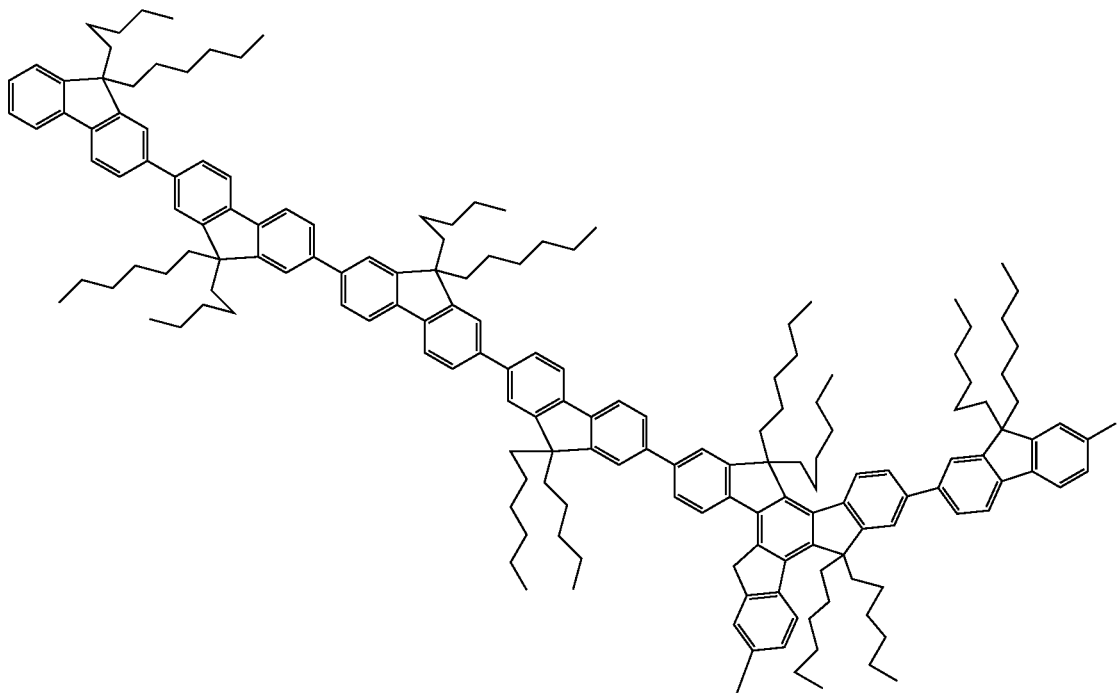
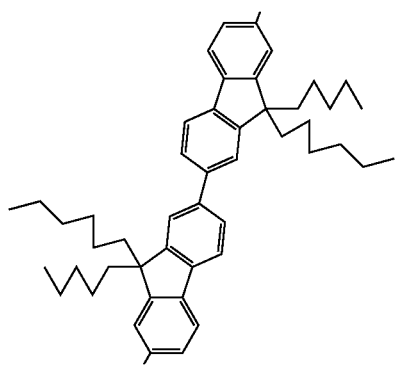
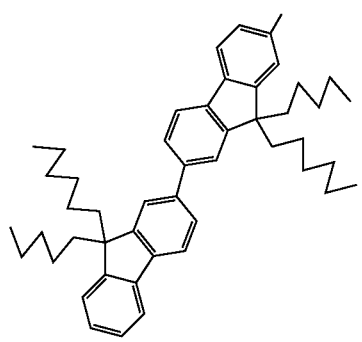

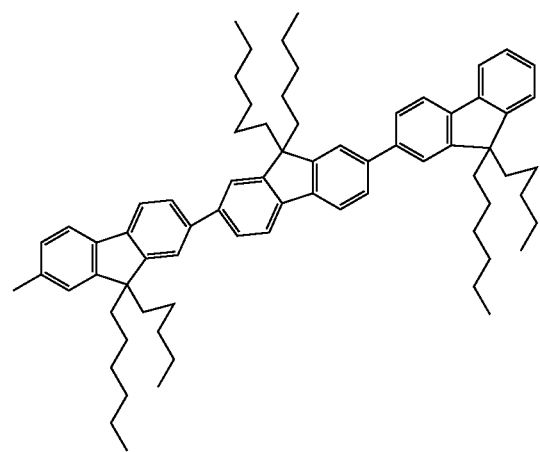
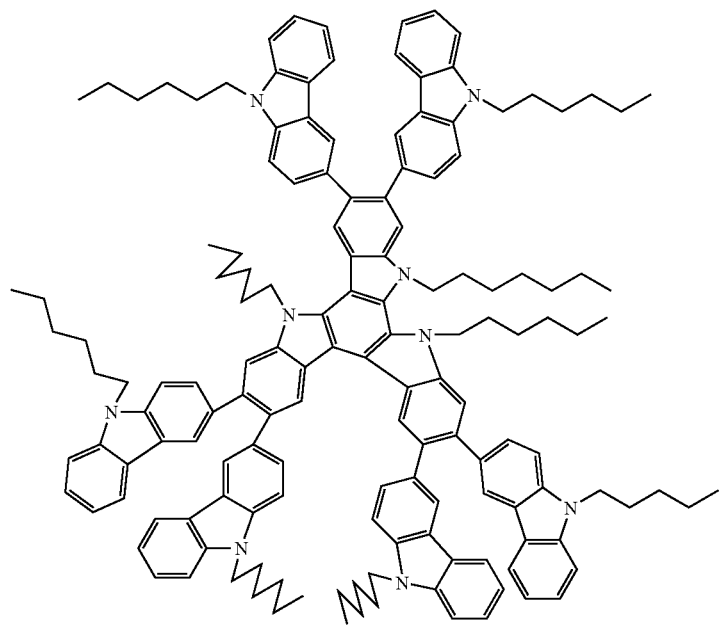
No. 15

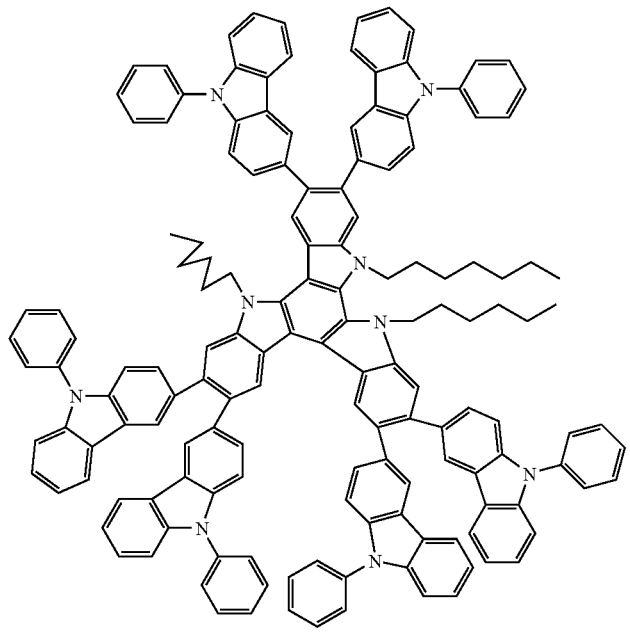

No. 16

On the other hand, the polymer material preferably has a molecular weight of 10,000 or more, and the molecular weight distribution of the material is not particularly limited.

In particular, it is preferable that the polymer material used in the organic light-emitting device of the present invention is a n-conjugated polymer. The n-conjugated polymer has high conductivity and can improve the injectability of carriers into the light-emitting layer. Accordingly, the emission efficiency of the device can be improved and the lifetime of the device can be lengthened. In addition, the n-conjugated polymer material has a light-emitting function, and hence light emission from the polymer material can be utilized.

Hereinafter, a part of the polymer material used in the organic light-emitting device of the present invention is exemplified, but the present invention is not limited thereto.

-continued

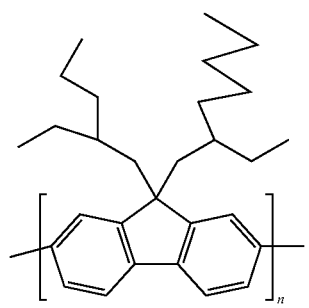

No. 102

No. 101

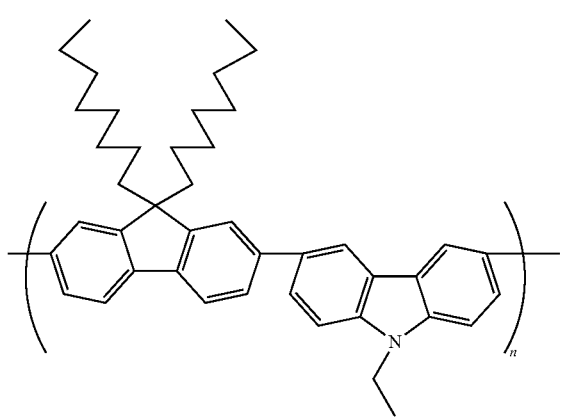

No. 103

No. 104

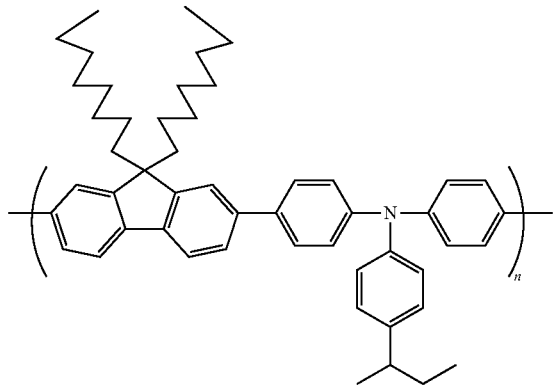

No. 105

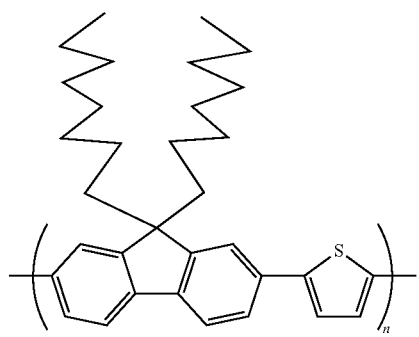

No. 106

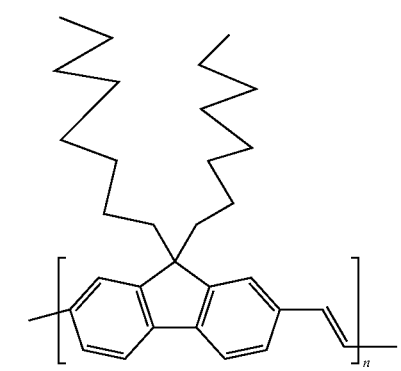

No. 107

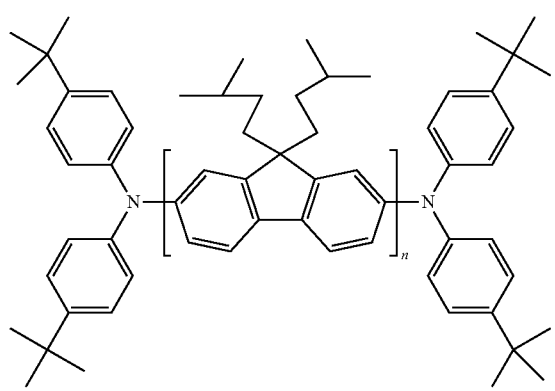

No. 108

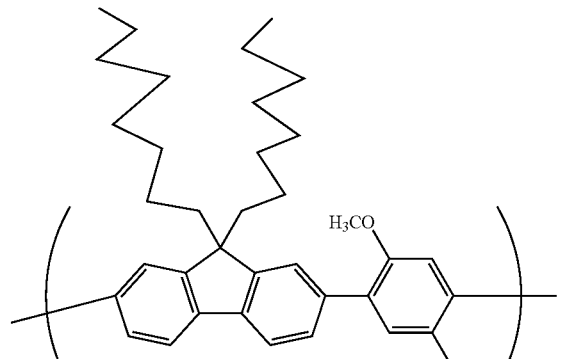

No. 109

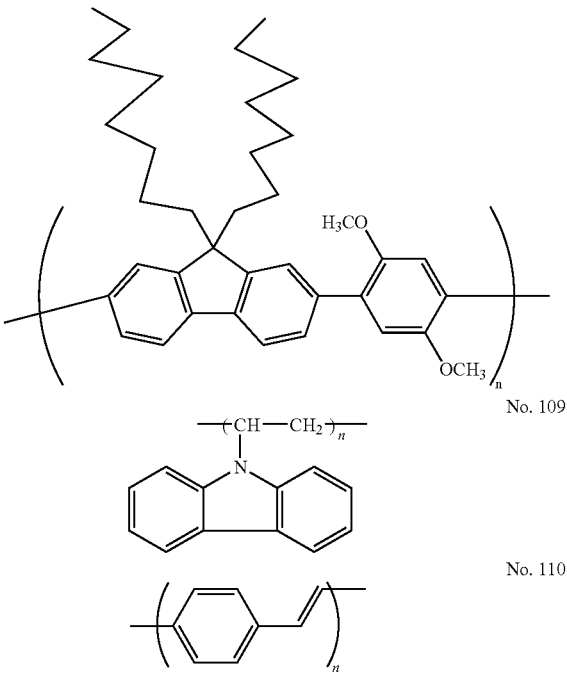

No. 110

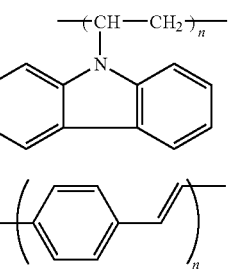

In the organic light-emitting device of the present invention, the light-emitting layer includes the oligomer material and the polymer material. The oligomer material has a high degree of freedom of material design as compared to polymer materials, and the purity of the material itself can be improved by purification. Therefore, by employing the oligomer material as a constituent material of the light-emitting layer, an organic light-emitting device having a high efficiency and a long lifetime can be provided. However, the oligomer material easily causes crystallization and aggregation as compared to polymer materials. Therefore, when a thin film is produced from only the oligomer, the quality of a formed film is not sufficiently stable. Here, the organic light-emitting device of the present invention includes a polymer material as a constituent material in addition to the oligomer material. Accordingly, the amorphous property of a film itself which constitutes the light-emitting layer is improved, whereby the crystallization and aggregation involved in the use of the oligomer material can be prevented. As a result, an organic light-emitting device having a higher efficiency and a longer lifetime can be obtained.

In addition, in the organic light-emitting device of the present invention, by appropriately selecting the oligomer material and the polymer material, the HOMO level, LUMO level, electron mobility, and hole mobility of the light-emitting layer can be suitably adjusted, whereby the injectability of carriers into the light-emitting layer is improved. Owing to the improvement of the injectability of carriers into the light-emitting layer, electric charge accumulated at the interfacial portions can be reduced, whereby the efficiency and lifetime of the device can be further improved.

Here, because the molecular size of the oligomer material is smaller than that of the polymer material, the oligomer material has good compatibility with the polymer material. Accordingly, the range of the selection of the material that can be mixed and the range of the available mixing ratio of the material can be increased. In addition, because the molecular weight of the oligomer material is larger than that of low-molecular materials, the oligomer material hardly causes crystallization and aggregation as compared to low-molecular materials. Accordingly, a large amount of the oligomer material can be mixed in the polymer material in such a degree that crystallization and aggregation are caused when a low-molecular material is used.

As described above, by mixing the polymer material and the oligomer material, the injectability of carriers into the light-emitting layer can be easily improved as compared to conventional technology, whereby the efficiency and lifetime of the device can be further improved.

Moreover, in the present invention, because a plurality of materials are used in the light-emitting layer, the injectability of carriers into the light-emitting layer can be improved and the lifetime of the device can be lengthened by mixing a polymer material having high hole injection property and an oligomer material having high electron injection property, for example.

In the organic light-emitting device of the present invention, the ratio of the oligomer material to the polymer material contained in the light-emitting layer is not particularly limited and can be selected appropriately in accordance with the intended purpose such as increase of carrier injection amount or improvement of the film quality. The weight ratio of the oligomer material to the polymer material is preferably 0.01 wt % to 80 wt % and more preferably 0.05 wt % to 50 wt % of the polymer material with respect to the total weight of the oligomer material and the polymer material.

Incidentally, because the oligofluorene compound used as the oligomer material has electron-transporting property, the oligofluorene compound can be used as a constituent material in layers other than a light-emitting layer, such as an electron injection layer or an electron-transporting layer.

In addition, in the organic light-emitting device of the present invention, a light-emitting dopant may be separately added, in addition to the oligomer material and the polymer material, as a constituent material of the light-emitting layer, and light may be emitted from the light-emitting dopant. In this case, as the light-emitting dopant material, any one of a singlet light-emitting material and a triplet light-emitting material can be used, but the triplet light-emitting material which emits light at a higher efficiency is preferably used. By incorporating the triplet light-emitting material into the light-emitting layer, the organic light-emitting device of the present invention can employ light emission from a triplet. As a result, an organic light-emitting device having higher emission efficiency can be provided.

Hereinafter, as examples of the triplet light-emitting material, the following compounds are given, but the present invention is not limited thereto.

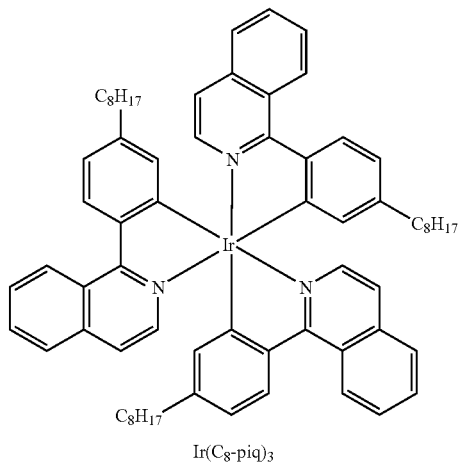

Ir(C$_8$-piq)$_3$

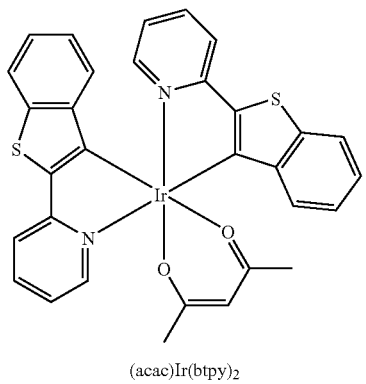

(acac)Ir(btpy)$_2$

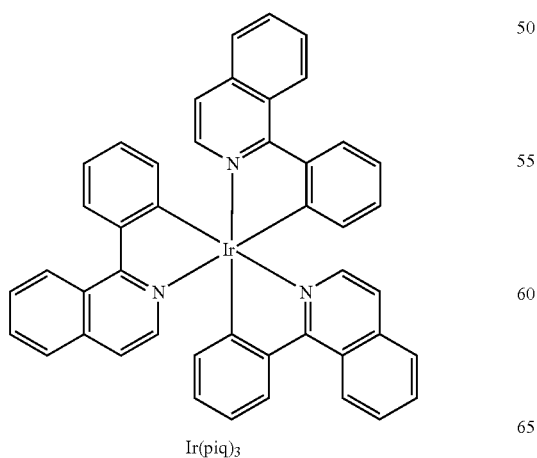

Ir(piq)$_3$

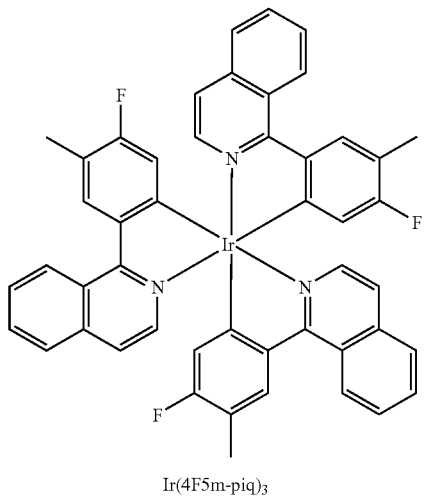

Ir(4F5m-piq)$_3$

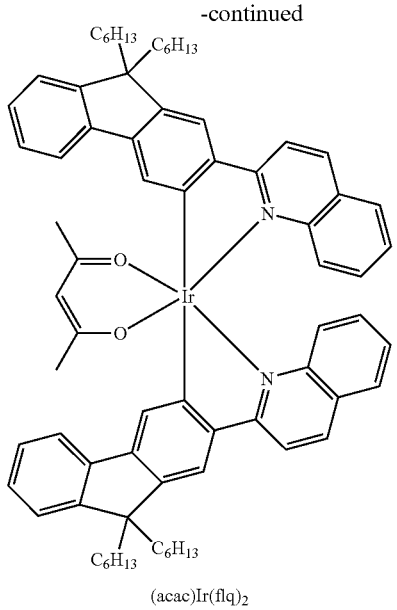

(acac)Ir(flq)₂

Next, other members which constitute the organic light-emitting device of the present invention will be described.

The material which constitutes the substrate 1 is, for example, glass, ceramic, semiconductor, metal, or plastic, but is not particularly limited thereto. When the structure of the device is of a bottom emission type, a transparent substrate such as a glass substrate is used. On the other hand, when the structure of the device is of a top emission type, a metal substrate is used, or a cathode material such as Ag is formed on a glass substrate or the like so as to form a mirror structure in order that light may be prevented from leaking to the lower portion of the substrate. In addition, the emission color can be controlled by additionally providing a color filter film, a fluorescent color conversion filter film, a dielectric reflection film, or the like to the substrate. Further, a thin film transistor (TFT) may be produced on a substrate and the device may be produced so as to connect thereto.

The constituent material of the anode 2 preferably has as large a work function as possible. Examples of the material include elemental metals such as gold, platinum, silver, copper, nickel, palladium, cobalt, selenium, vanadium, tungsten or chromium, or alloys thereof; metal oxides such as tin oxide, zinc oxide, indium oxide, indium tin oxide (ITO), and indium zinc oxide, and halides such as CuI. Further, a conductive polymer such as polyaniline, polypyrrole, polythiophene, or polyphenylene sulfide may also be used. One kind of these electrode substances may be used alone, or two or more kinds of them may be used in combination. Further, the anode may be constituted of either a single layer or plural layers.

As the constituent material of the hole injection layer 3, any material having hole-transporting property can be used. In the organic light-emitting device of the present invention, a material is preferred which is advantageously used in production of a coating organic light-emitting device and has resistance to a solvent that dissolves a constituent material of the light-emitting layer 4. Examples of the material constituting the hole injection layer 3 include, but not limited to, phthalocyanine derivatives, naphthalocyanine derivatives, and porphyrin derivatives; oxazole, oxadiazole, triazole, imidazole, imidazolone, pyrazoline, tetrahydroimidazole, polyarylalkane, butadiene, benzidine-type triphenylamine, styrylamine-type triphenylamine, diamine-type triphenylamine, and derivatives thereof; and polymer materials such as polyvinylcarbazole, polysilane, and PEDOT:PSS.

Examples of the constituent material of the electron injecting layer 5 include a fluoride, carbonate compound, or oxide of an alkali metal or alkaline earth metal such as typified by LiF, $CsCO_3$, or CaO. Further, even an organic compound having electron-transporting property can also be employed in the organic light-emitting device of the present invention.

The material constituting the cathode 6 preferably has a low work function, and include, for instance an elemental metal such as lithium, sodium, potassium, calcium, magnesium, aluminum, indium, ruthenium, titanium, manganese, yttrium, silver, lead, tin, and chromium; or an alloy made of a plurality of the above metals, such as lithium-indium, sodium-potassium, magnesium-silver, aluminum-lithium, aluminum-magnesium, and magnesium-indium. Further, a metal oxide such as indium tin oxide (ITO) can be also used. These electrode materials can be used singly or in combination. In addition, the cathode may be either of a single layer configuration or of a multilayer configuration.

Incidentally, at least one of the anode 2 and the cathode 6 is desirably either transparent or translucent.

In addition, as described above, in the organic light-emitting device of the present invention, a hole-transporting layer or an electron-transporting layer may further be provided. Here, as the materials which constitute a hole-transporting layer and an electron-transporting layer, any material can be used as long as it has hole-transporting property or electron-transporting property, respectively. For example, the constituent material of the hole injection layer 3 and the constituent material of the electron injection layer 5 can be used, respectively.

Incidentally, in the organic electroluminescent device of the present invention, the produced device may be provided with a protective layer or an encapsulation layer, for the purpose of preventing contact with oxygen or moisture. Examples of such a protective layer include a diamond thin film; a film of an inorganic material such as a metal oxide and a metal nitride; a film of a polymer such as a fluororesin, polyparaxylene, polyethylene, silicone resin, and polystyrene resin; and further a film of a photocurable resin. Further, the produced device may also be covered with glass, a gas-impermeable film or a metal, or be packaged with a suitable encapsulation resin.

When the organic light-emitting device of the present invention is produced, a thin film serving as the light-emitting layer 4 is formed by a coating process. Specific examples of the thin film forming process by coating includes a spin coating method, a slit coating (slot coating) method, a printing method, an ink jet method, a dispense method, a spraying method, and a nozzle printing method.

In the case of forming a thin film serving as the light-emitting layer 4 by a coating process, any solvent can be used as long as it dissolves organic materials (oligomer material and polymer material) which constitute the light-emitting layer 4. One kind of solvent may be used alone or two or more kinds of solvents may be used in combination. Here, in the case where the thin film is patterned using an ink jet method, a dispense method, or a nozzle printing method, when a solvent having a low boiling point is used, there are posed such problems that nozzles are clogged, and stable coating cannot be performed because of the surface tension being small. Accordingly, it is preferred to use a solvent having a boiling point of 100° C. or more.

The organic light-emitting device of the present invention is applicable to a product which requires energy conservation and high luminance. As application examples, an image display apparatus, a light source of a printer, an illumination apparatus, a backlight of a liquid crystal display apparatus, and the like are conceivable.

An example of the image display apparatus includes an energy-saving, light-weight flat panel display with high visibility.

Further, as the light source of a printer, for example, a laser light source portion of a laser beam printer that has been currently used widely can be replaced by the organic light-emitting device of the present invention. An example of a replacement method includes a method of placing an organic light-emitting device that can be addressed independently on an array. Even if the laser light source portion is replaced by the organic light-emitting device of the present invention, there is no particular difference in the formation of an image from a conventional example by conducting desired light exposure to a photosensitive drum. The volume of an apparatus can be reduced remarkably by using the organic light-emitting device of the present invention.

Regarding the illumination apparatus and the backlight, the effect of saving energy can be expected by using the organic light-emitting device of the present invention.

Next, the display apparatus using the organic light-emitting device of the present invention will be described. Hereinafter, the display apparatus of the present invention will be described in detail by exemplifying an active matrix system with reference to the accompanying drawings.

Figure 4:
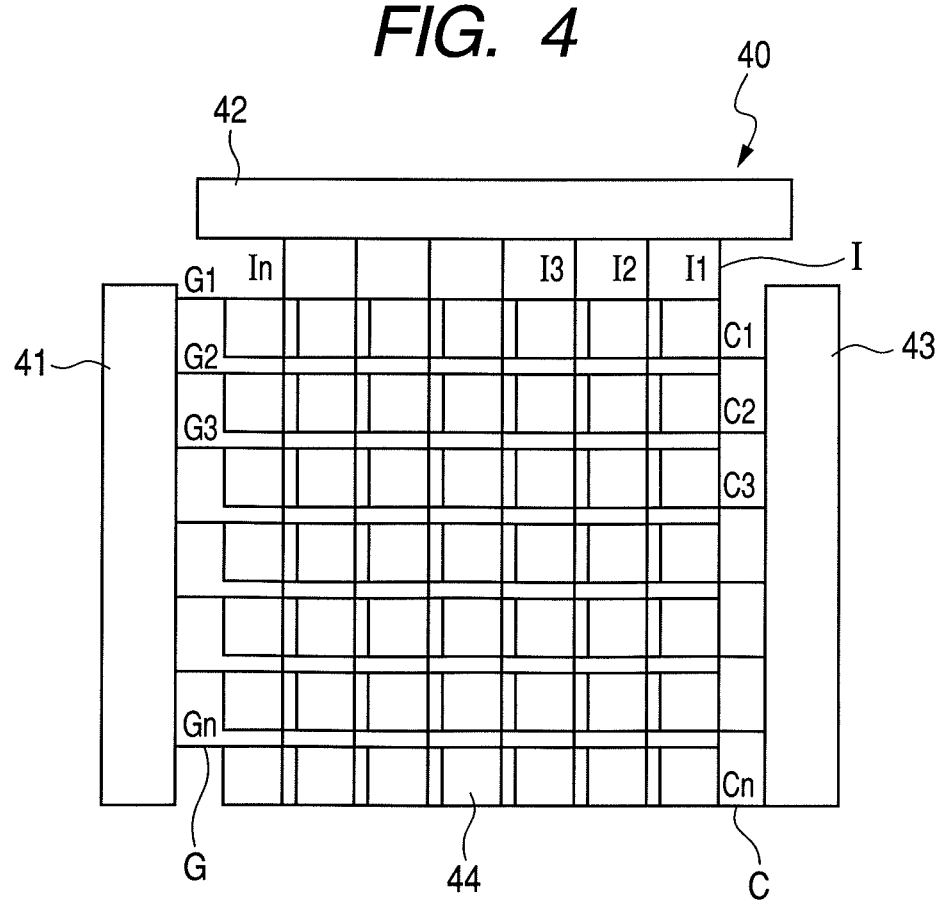
FIG. 4 is a schematic plan view illustrating a structural example of a display apparatus having an organic light-emitting device of the present invention and a drive unit.

FIG. 4 is a view schematically illustrating a constitution of a display apparatus according to an embodiment of the present invention including the organic light-emitting device of the present invention and a driving unit. In a display apparatus 40 illustrated in FIG. 4, a scanning signal driver 41, an information signal driver 42, and a current supply source 43 are disposed, which are each connected to gate selection lines G, information signal lines I, and current supply lines C. A pixel circuit 44 is disposed at a crossing point of the gate selection line G and the information signal line I. The scanning signal driver 41 successively selects gate selection lines G1, G2, G3, . . . or Gn, and in synchronization therewith, an image signal is applied from the information signal driver 42 to the pixel circuit 44 through any of the information signal lines I1, I2, I3, . . . or In.

Next, the operation of the pixel will be described.

Figure 5:
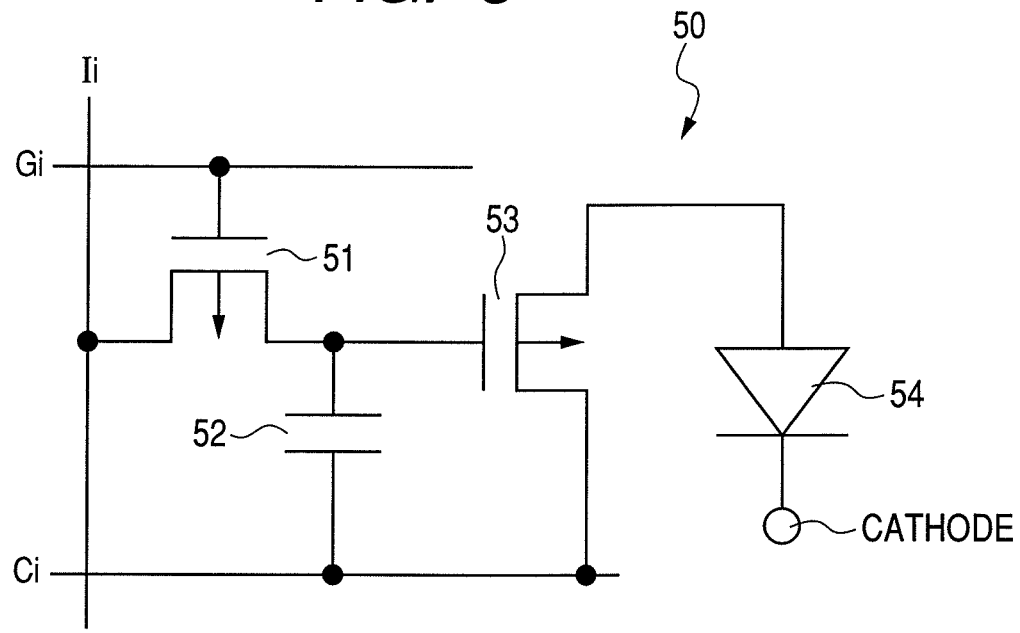
FIG. 5 is a circuit diagram illustrating a circuit which constitutes one pixel disposed in the display apparatus of FIG. 4.

FIG. 5 is a circuit diagram illustrating a circuit constituting one pixel disposed in the display apparatus shown in FIG. 4. In a pixel circuit 50 of FIG. 5, when a selection signal is applied to the gate selection line G1, a first thin film transistor (TFT1) 51 is turned on, and an image signal Ii is supplied to a capacitor ($C_{add}$) 52, whereby a gate voltage of a second thin film transistor (TFT2) 53 is determined. A current is supplied to an organic light-emitting device 54 from a current supply line Ci according to a gate voltage of the second thin film transistor (TFT2) 53. The gate potential of the second thin film transistor (TFT2) 53 is held at the capacitor ($C_{add}$) 52 until the first thin film transistor (TFT1) 51 is scanned and selected next. Therefore, a current continues to flow through the organic light-emitting device 54 until the subsequent scanning is conducted. This enables the organic light-emitting device 54 to emit light at all times during one frame.

Figure 6:
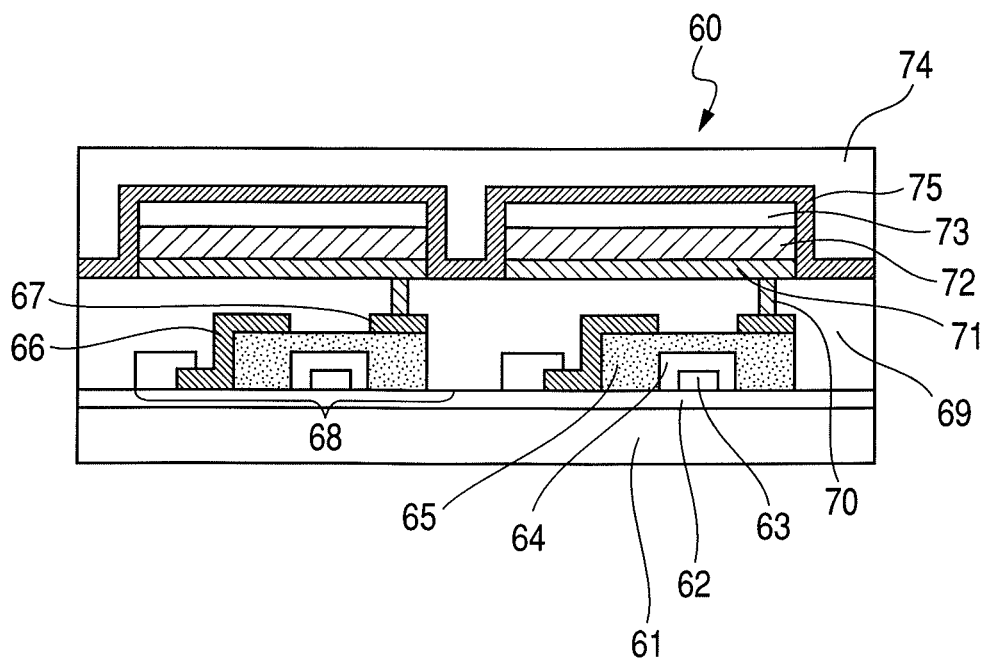
FIG. 6 is a schematic cross-sectional view illustrating an example of a structure of a TFT substrate.

FIG. 6 is a schematic view illustrating an example of a cross-sectional structure of a TFT substrate used in the display apparatus of FIG. 4. The detail of the structure will be described by way of an example of the production process of a TFT substrate. When the display apparatus 60 of FIG. 6 is produced, a substrate 61 formed of glass or the like is coated with a moisture resistant film 62 for protecting a member (a TFT or an organic layer) formed in an upper portion. As a material constituting the moisture resistant film 62, silicon oxide, a composite of silicon oxide and silicon nitride, or the like is used. Next, a metal such as Cr is formed into a film by sputtering and patterned to a predetermined circuit shape, whereby a gate electrode 63 is formed. Subsequently, silicon oxide or the like is formed into a film by a plasma CVD, a catalyst chemical vapor deposition (cat-CVD), or the like, and patterned to form a gate insulating film 64. Next, a silicon film is formed by a plasma CVD (by annealing at a temperature of 290° C. or higher in some cases), and patterned according to a circuit shape, whereby a semiconductor layer 65 is formed.

Further, a drain electrode 66 and a source electrode 67 are provided on the semiconductor film 65 to produce a TFT element 68, whereby a circuit as illustrated in FIG. 5 is formed. Next, an insulating film 69 is formed in an upper portion of the TFT element 68. Next, a contact hole (through-hole) 70 is formed so that an anode 71 for an organic light-emitting device formed of a metal comes into contact with the source electrode 67.

A multi-layer or single-layer organic layer 72 and a cathode 73 are successively laminated on the anode 71, whereby a display apparatus 60 can be obtained. At this time, in order to prevent the degradation of the organic light-emitting device, a first protective layer 74 and a second protective layer 75 may be provided. By driving the display apparatus using the fluorene compound of the present invention, a display of a satisfactory quality, which is stable for a display for a long period of time, can be conducted.

In the display apparatus, there is no particular limit to a switching element, and any switching element can be easily applied to a single crystal silicon substrate, an MIM element, an a-Si type, and the like.

EXAMPLES

Hereinafter, the present invention will be described in detail below with reference to examples. However, the present invention is not limited thereto.

Synthesis Example 1

Synthesis of Exemplified Compound No. 2

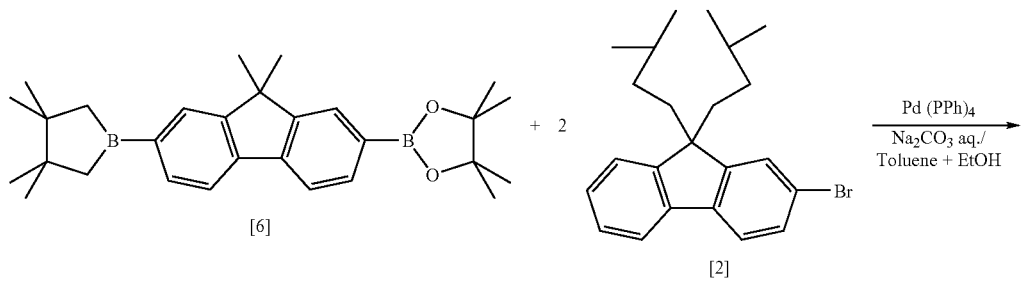

-continued
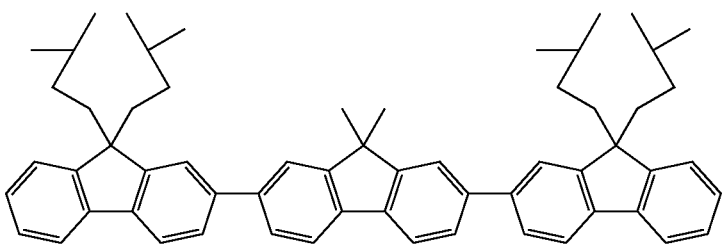
[87% yield]
[7]
[7] + Br₂ →(FeCl₃/CHCl₃)
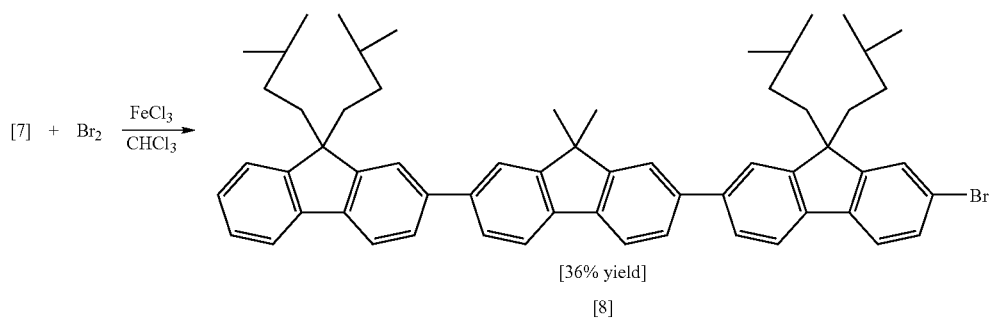
[36% yield]
[8]
[8] + HB(pinacol) →(Ni(dppp)Cl₂ / Et₃N/Toluene)
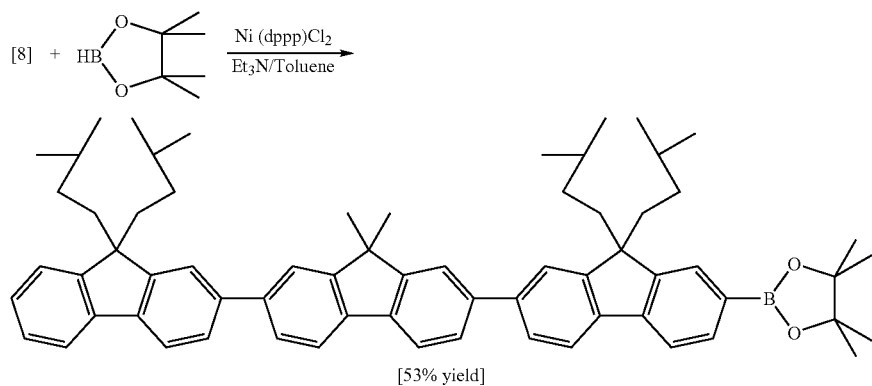
[53% yield]
[9]
[7] + 2Br₂ →(FeCl₃/CHCl₃)
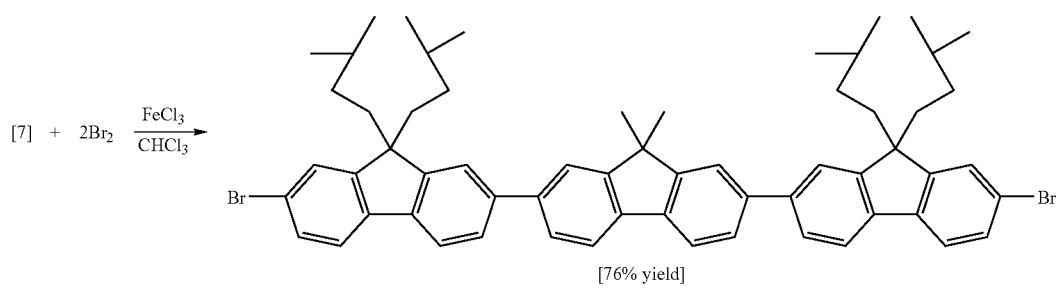
[76% yield]
[10]
[10] + 2 [9] →(Pd(PPh₃)₄ / Na₂CO₃ aq./ Toluene + EtOH)
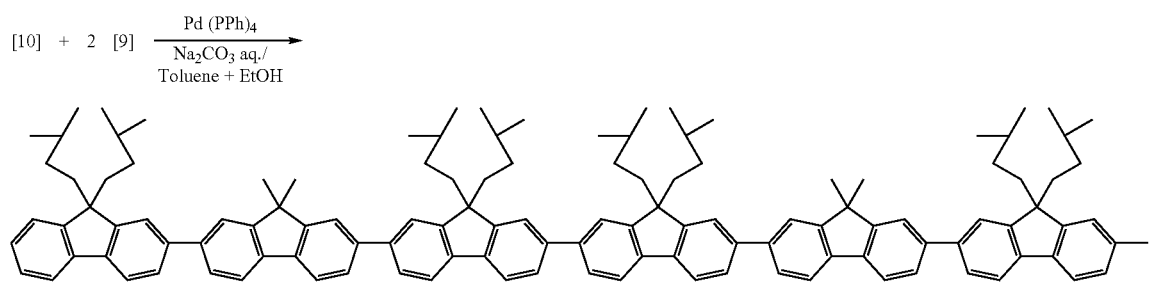

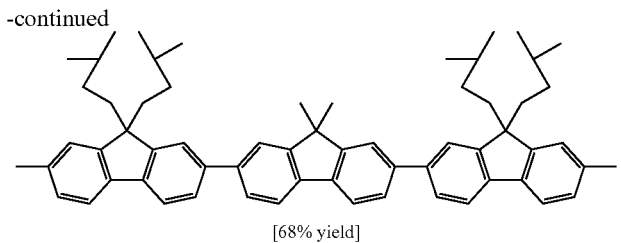

[68% yield]
Exemplified Compound No. 2

(1) The following reagents and solvents were place in a 2000 ml three-necked flask.
  Dipinacol body [6]: 20 g (42.2 mmol)
  Monobromo body [2]: 39.0 g (101 mmol)
  Toluene: 600 ml
  Ethanol: 200 ml Next, an aqueous solution prepared by dissolving 40 g of sodium carbonate in 200 ml of water was added dropwise to the reaction solution while the reaction solution was stirred in a nitrogen atmosphere at room temperature. Subsequently, 2.4 g (2.2 mmol) of tetrakis(triphenylphosphine)palladium (0) was added to the reaction solution. Next, after the reaction solution was stirred at room temperature for 30 minutes, the temperature of the reaction solution was increased to 77° C., and then, the reaction solution was stirred for 5 hours. After the completion of the reaction, the organic layer of the reaction solution was extracted with chloroform and dried with anhydrous sodium sulfate. After the solvent was evaporated under reduced pressure, the remainder was purified by silica gel column chromatography (developing solvent: hexane/toluene mixed solvent), whereby 29.4 g of a fluorene trimer [7] as a white crystal was obtained (87% yield).

(2) 10.0 g (12.5 mmol) of the fluorene trimer [7] and 200 ml of chloroform were placed in a 500-ml three-necked flask. Next, after the reaction solution was cooled to 5° C., 0.1 g (0.63 mmol) of iron chloride was added to the reaction solution. Next, after a mixed solution prepared by mixing 4.4 g (27.3 mmol) of bromine and 50 ml of chloroform was added dropwise to the reaction solution, the temperature of the reaction solution was increased to room temperature, and then, the reaction solution was stirred for 8 hours. After the completion of the reaction, the organic layer of the reaction solution was extracted with chloroform, washed with an aqueous solution of sodium thiosulfate, and dried with anhydrous sodium sulfate. After the solvent was evaporated under reduced pressure, the remainder was purified by silica gel column chromatography (developing solvent: heptane/toluene mixed solvent), whereby 9.1 g of a dibromofluorene trimer [10] as a white crystal was obtained (76% yield).

(3) 10.0 g (12.5 mmol) of the fluorene trimer [7] and 200 ml of chloroform were placed in a 500-ml three-necked flask. Next, after the reaction solution was cooled to 5° C., 0.1 g (0.63 mmol) of iron chloride was added to the reaction solution. Next, after a mixed solution prepared by mixing 2.2 g (13.8 mmol) of bromine and 50 ml of chloroform was added dropwise to the reaction solution, the temperature of the reaction solution was increased to room temperature, and then, the reaction solution was stirred for 8 hours. After the completion of the reaction, the organic layer of the reaction solution was extracted with chloroform, washed with an aqueous solution of sodium thiosulfate, and dried with anhydrous sodium sulfate. After the solvent was evaporated under reduced pressure, the remainder was purified by silica gel column chromatography (developing solvent: heptane/toluene mixed solvent), whereby 4.0 g of a monobromofluorene trimer [8] as a white crystal was obtained (36% yield).

(4) 3.0 g (3.4 mmol) of the monobromofluorene trimer [8] and 100 ml of toluene were placed in a 200-ml three-necked flask. Next, 2.5 ml (18 mmol) of triethylamine and 0.13 g (0.24 mmol) of (1,3-diphenylphosphinopropane)dichloronickel were added to the reaction solution while the reaction solution was stirred in a nitrogen atmosphere at room temperature. Next, after 2.6 ml (18 mmol) of 4,4,5,5-tetramethyl-1,3,2-dioxaborolane was added dropwise to the reaction solution, the reaction solution was stirred at 100° C. for 5 hours. After the completion of the reaction, the organic layer of the reaction solution was extracted with ethyl acetate and dried with anhydrous sodium sulfate. After the solvent was evaporated under reduced pressure, the remainder was purified by silica gel column chromatography (developing solvent: hexane/toluene mixed solvent), whereby 1.7 g of a monopinacolfluorene trimer [9] as a white crystal was obtained (53% yield).

(5) The following reagents and solvents were placed in a 200-ml three-necked flask.
  Dibromofluorene trimer [10]: 1.0 g (1.04 mmol)
  Monopinacolfluorene trimer [9]: 2.1 g (2.29 mmol)
  Toluene: 80 ml
  Ethanol: 40 ml Next, an aqueous solution prepared by dissolving 2 g of sodium carbonate in 10 ml of water was added dropwise to the reaction solution while the reaction solution was stirred in a nitrogen atmosphere at room temperature. Subsequently, 0.06 g (0.05 mmol) of tetrakis(triphenylphosphine)palladium (0) was added to the reaction solution. Next, after the reaction solution was stirred at room temperature for 30 minutes, the temperature of the reaction solution was increased to 77° C., and then, the reaction solution was stirred for 5 hours. After the completion of the reaction, the organic layer of the reaction solution was extracted with chloroform and dried with anhydrous sodium sulfate. After the solvent was evaporated under reduced pressure, the remainder was purified by silica gel column chromatography (developing solvent: hexane/toluene mixed solvent), whereby 1.7 g of Exemplified Compound No. 2 as a yellowish white crystal was obtained (68% yield). The purity of the obtained Exemplified Compound No. 2 was 99.9 wt % and its molecular weight was 2,488.

Synthesis Example 2
Synthesis of Exemplified Compound No. 3
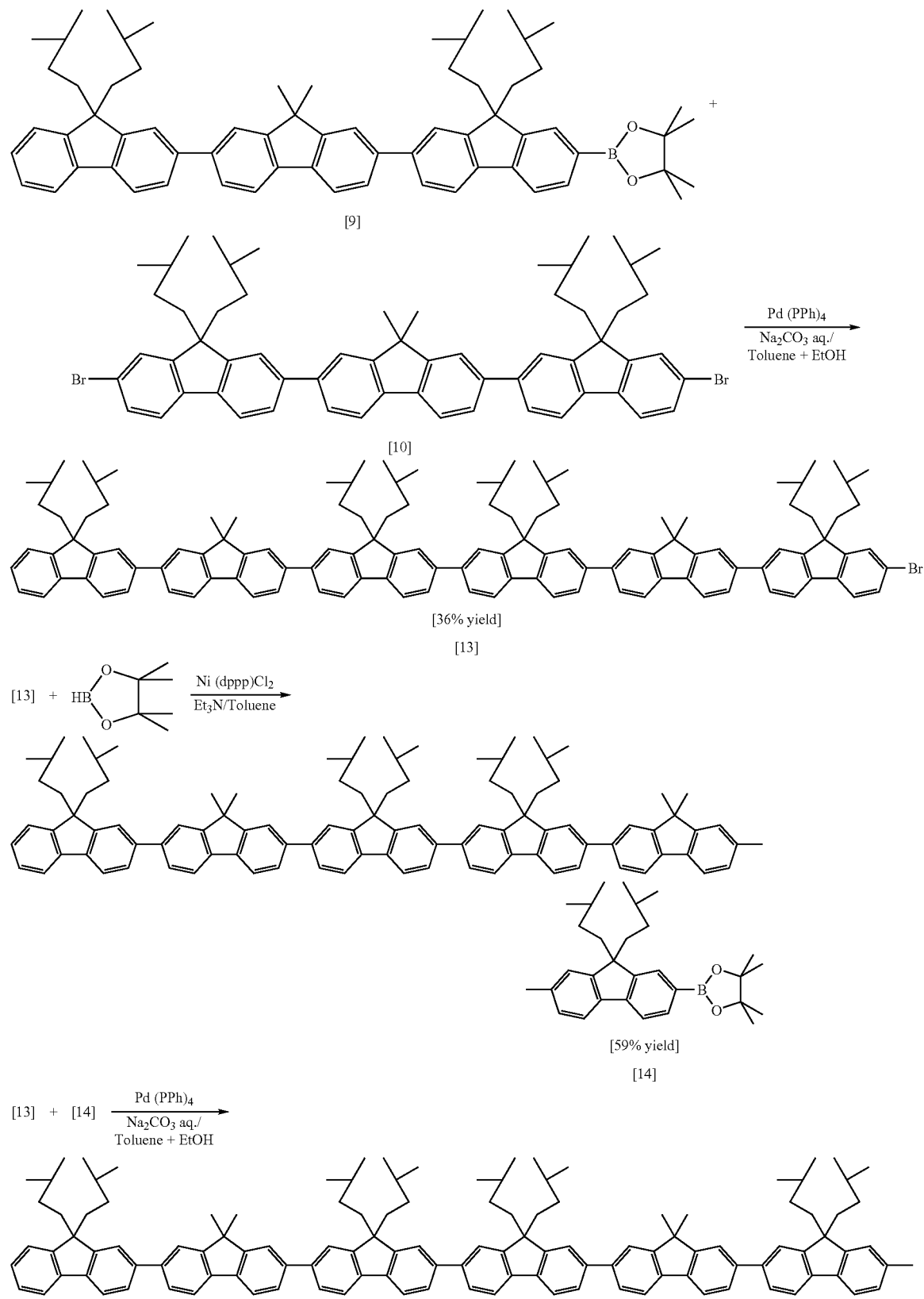

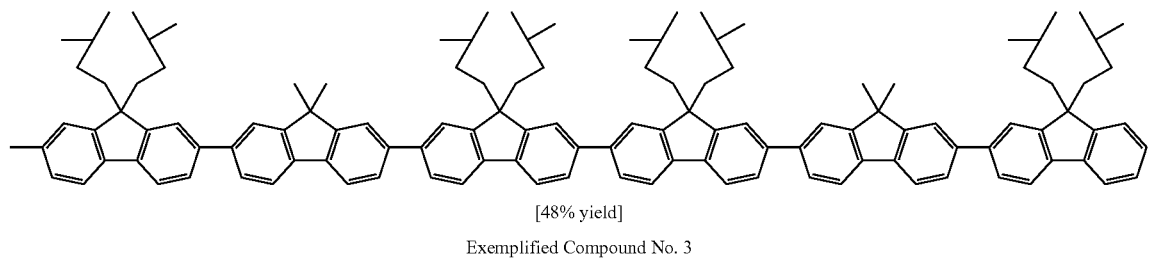

[48% yield]

Exemplified Compound No. 3

(1) The following reagents and solvents were placed in a 500-ml three-necked flask.

Monopinacolfluorene trimer [9]: 9.7 g (10.4 mmol)
Dibromofluorene trimer [10]: 10 g (10.4 mmol)
Toluene: 250 ml
Ethanol: 80 ml Next, an aqueous solution prepared by dissolving 20 g of sodium carbonate in 100 ml of water was added dropwise to the reaction solution while the reaction solution was stirred in a nitrogen atmosphere at room temperature. Subsequently, 0.58 g (0.5 mmol) of tetrakis(triphenylphosphine)palladium (0) was added to the reaction solution. Next, after the reaction solution was stirred at room temperature for 30 minutes, the temperature of the reaction solution was increased to 77° C., and then, the reaction solution was stirred for 5 hours. After the completion of the reaction, the organic layer of the reaction solution was extracted with chloroform and dried with anhydrous sodium sulfate. After the solvent was evaporated under reduced pressure, the remainder was purified by silica gel column chromatography (developing solvent: hexane/toluene mixed solvent), whereby 6.3 g of a monobromofluorene hexamer [13] as a yellowish white crystal was obtained (36% yield).

(2) 4.0 g (2.4 mmol) of the monobromofluorene hexamer [13] and 100 ml of toluene were placed in a 300-ml three-necked flask. Next, 0.5 ml (3.6 mmol) of triethylamine and 0.13 g (0.24 mmol) of (1,3-diphenylphosphinopropane) dichloronickel were added to the reaction solution while the reaction solution was stirred in a nitrogen atmosphere at room temperature. Next, after 0.52 ml (3.6 mmol) of 4,4,5,5-tetramethyl-1,3,2-dioxaborolane was dropped to the reaction solution, the reaction solution was stirred at 100° C. for 10 hours. After the completion of the reaction, the organic layer of the reaction solution was extracted with ethyl acetate and dried with anhydrous sodium sulfate. After the solvent was evaporated under reduced pressure, the remainder was purified by silica gel column chromatography (developing solvent: hexane/toluene mixed solvent), whereby 2.4 g of a monopinacolfluorene hexamer [14] as a yellowish white crystal was obtained (59% yield).

(3) The following reagents and solvents were placed in a 200-ml three-necked flask.

Monobromofluorene hexamer [13]: 1.0 g (0.59 mmol)
Monopinacolfluorene hexamer [14]: 1.03 g (0.59 mmol)
Toluene: 80 ml
Ethanol: 30 ml Next, an aqueous solution prepared by dissolving 1.2 g of sodium carbonate in 6 ml of water was added dropwise to the reaction solution while the reaction solution was stirred in a nitrogen atmosphere at room temperature. Subsequently, 0.03 g (0.03 mmol) of tetrakis(triphenylphosphine)palladium (0) was added to the reaction solution. After the reaction solution was stirred at room temperature for 30 minutes, the temperature of the reaction solution was increased to 77° C., and then, the reaction solution was stirred for 5 hours. After the completion of the reaction, the organic layer of the reaction solution was extracted with chloroform and dried with anhydrous sodium sulfate. After the solvent was evaporated under reduced pressure, the remainder was purified by silica gel column chromatography (developing solvent: hexane/toluene mixed solvent), whereby 0.91 g of Exemplified Compound No. 3 as a yellowish white crystal was obtained (48% yield). The purity of the obtained Exemplified Compound No. 3 was 99.9 wt % and its molecular weight was 3,316.

Synthesis Example 3

Synthesis of Exemplified Compound No. 12

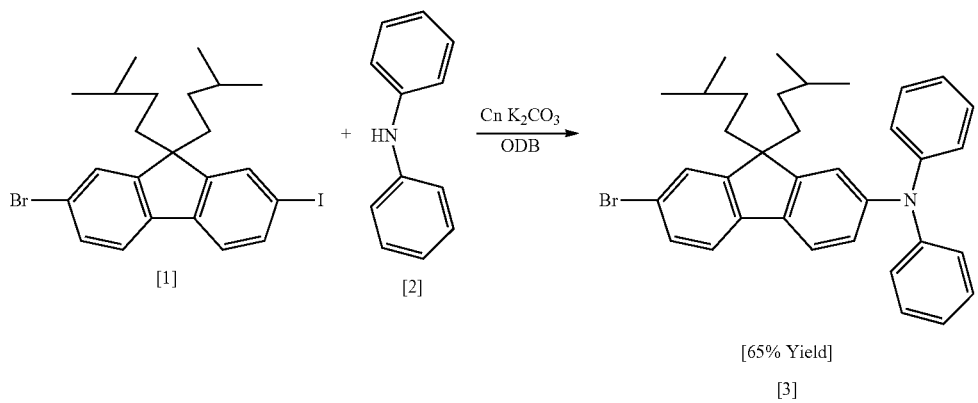

[65% Yield]

[3]

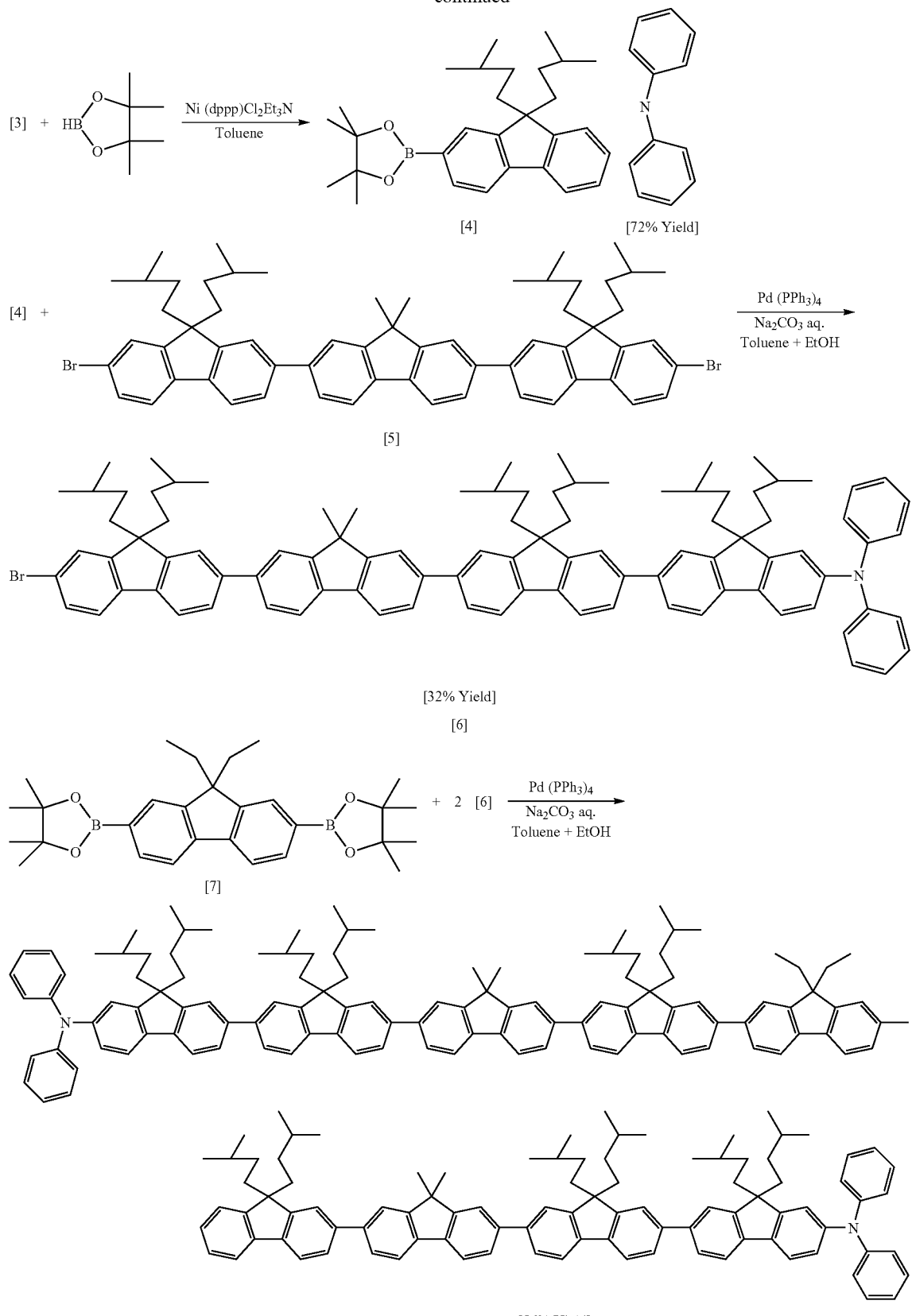
Exemplified Compound No. 12

(1) The following reagents and solvents were placed in a 500-ml three-necked flask.

2-bromo-7-iodofluorene [1]: 20 g (39.1 mmol)
    Diphenyl amine [2]: 6.6 g (39.1 mmol)
    Copper powder: 7.4 g (117 mmol)
    Potassium carbonate: 16.2 g (117 mmol)
    1,2-dichlorobenzene: 200 ml Next, the reaction solution was stirred at 180° C. for 12 hours. After the completion of the reaction, the reaction solution was filtered, and the organic layer of the reaction solution was extracted with chloroform and then dried with anhydrous sodium sulfate. After the solvent was evaporated under reduced pressure, the remainder was purified by silica gel column chromatography (developing solvent: hexane/toluene mixed solvent), whereby 14.0 g of an adduct [3] as a transparent liquid was obtained (65% yield).

(2) 10 g (18.1 mmol) of the adduct [3] and 100 ml of toluene were placed in a 300-ml three-necked flask. Next, 2.0 g (3.6 mmol) of $Ni(dppp)Cl_2$ and 7.6 ml (54.3 mmol) of triethyl amine were added while the reaction solution was stirred in a nitrogen atmosphere at room temperature. Subsequently, after 7.9 ml (54.3 mmol) of pinacolborane was poured in the reaction solution, the reaction solution was heated to reflux for 6 hours. After the completion of the reaction, water was poured therein, and the organic layer of the reaction solution was extracted with ethyl acetate and dried with anhydrous sodium sulfate. After the solvent was evaporated under reduced pressure, the remainder was purified by silica gel column chromatography (developing solvent: hexane and ethyl acetate mixed solvent), whereby 7.8 g of a pinacol body [4] as a transparent liquid was obtained (72% yield).

(3) The following reagents and solvents were placed in a 500-ml three-necked flask.

Pinacol body [4]: 5.0 g (8.3 mmol)
    Dibromo body [5]: 5.9 g (8.3 mmol)
    Toluene: 100 ml
    Ethanol: 50 ml Next, an aqueous solution prepared by dissolving 16 g of sodium carbonate in 80 ml of water was added dropwise to the reaction solution while the reaction solution was stirred in a nitrogen atmosphere at room temperature. Subsequently, 0.48 g (0.42 mmol) of tetrakis(triphenylphosphine)palladium (0) was added to the reaction solution. Next, the reaction solution was stirred under reflux for 3 hours. After the completion of the reaction, the organic layer of the reaction solution was extracted with toluene and dried with anhydrous sodium sulfate. After the solvent was evaporated under reduced pressure, the remainder was purified by silica gel column chromatography (developing solvent: hexane/toluene mixed solvent), whereby 3.3 g of a bromo body [6] as a yellow crystal was obtained (32% yield).

(4) The following reagents and solvents were placed in a 200-ml three-necked flask.

Dipinacol body [7]: 0.32 g (0.67 mmol)
    Bromo body [6]: 2.0 g (1.6 mmol)
    Toluene: 50 ml
    Ethanol: 20 ml Next, an aqueous solution prepared by dissolving 2 g of sodium carbonate in 10 ml of water was added dropwise to the reaction solution while the reaction solution was stirred in a nitrogen atmosphere at room temperature. Subsequently, 0.04 g (0.03 mmol) of tetrakis(triphenylphosphine)palladium (0) was added to the reaction solution. Next, the reaction solution was stirred under reflux for 3 hours. After the completion of the reaction, the organic layer of the reaction solution was extracted with toluene and dried with anhydrous sodium sulfate. After the solvent was evaporated under reduced pressure, the remainder was purified by silica gel column chromatography (developing solvent: hexane/toluene mixed solvent), whereby 0.96 g of an allylamino-substituted oligofluorene, which is Exemplified Compound No. 12, as a yellow crystal was obtained (56% yield). The purity of the obtained Exemplified Compound No. 12 was 99.9 wt % and its molecular weight was 3,004.

Synthesis Example 4

Synthesis of Exemplified Compound No. 9

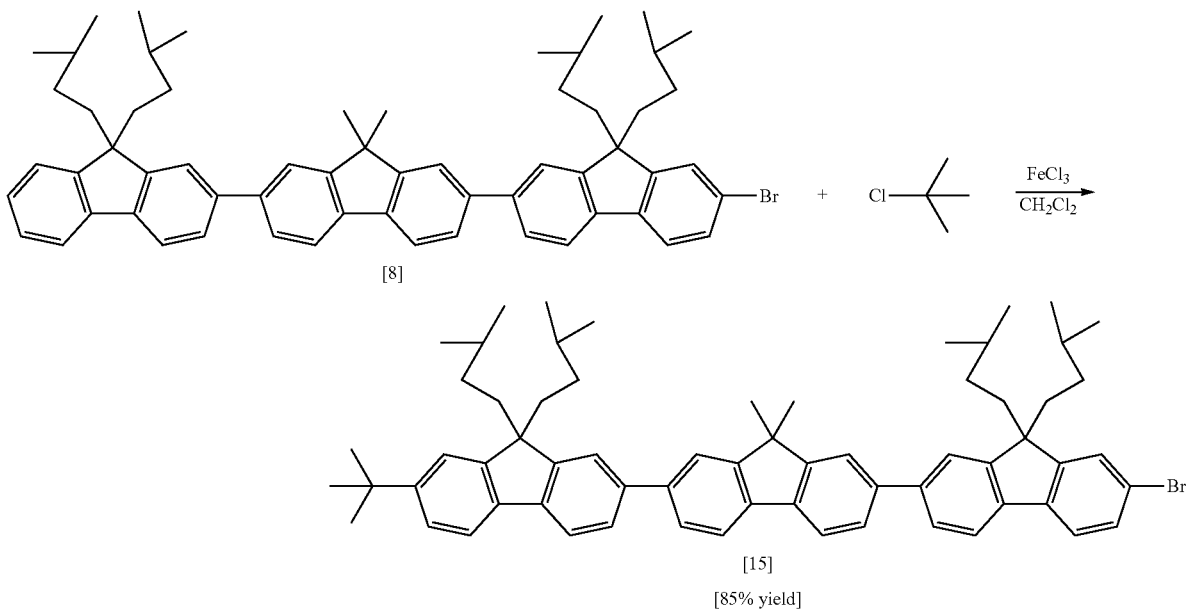

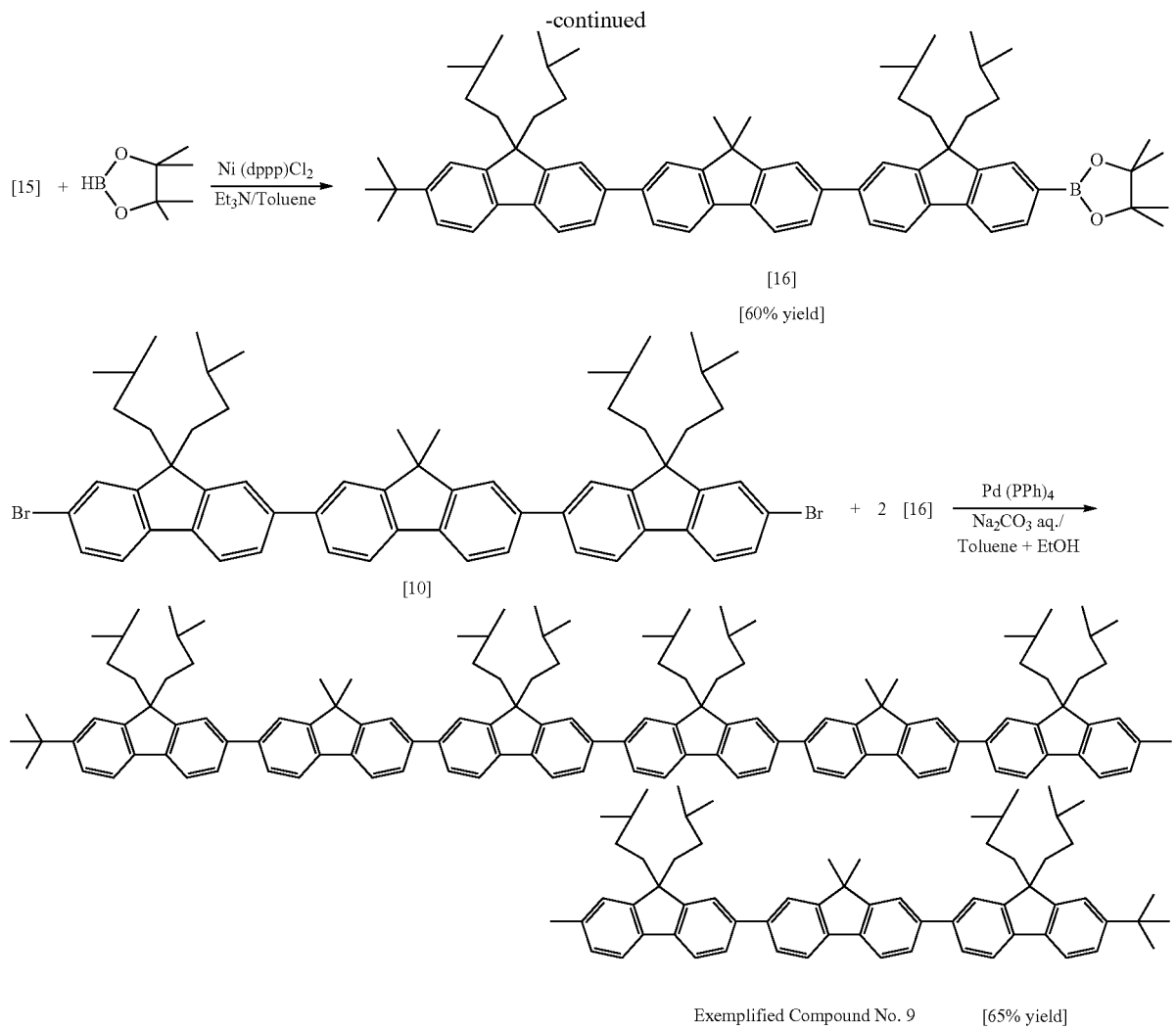

Exemplified Compound No. 9    [65% yield]

(1) 5.0 g (5.7 mmol) of monobromofluorene trimer [8] and 100 ml of dichloromethane were placed in a 300-ml three-necked flask. Next, 0.56 g (6.0 mmol) of t-butylchloride and 10 ml of dichloromethane were added dropwise to the reaction solution while the reaction solution was stirred in a nitrogen atmosphere at 0° C. Next, the temperature of the reaction solution was increased gradually to room temperature, and then stirred for 12 hours. After the completion of the reaction, water was added, and the organic layer of the reaction solution was extracted with chloroform and dried with anhydrous sodium sulfate. After the solvent was evaporated under reduced pressure, the remainder was purified by silica gel column chromatography (developing solvent: hexane/toluene mixed solvent), whereby 4.5 g of a monobromofluorene trimer [15] as a yellowish white crystal was obtained (85% yield).

(2) 3.0 g (3.2 mmol) of the monobromofluorene trimer [15] and 100 ml of toluene were placed in a 200-ml three-necked flask. Next, 2.5 ml (18 mmol) of triethylamine and 0.13 g (0.24 mmol) of (1,3-diphenylphosphinopropane)dichloronickel were added to the reaction solution while the reaction solution was stirred in a nitrogen atmosphere at room temperature. Next, after 2.6 ml (18 mmol) of 4,4,5,5-tetramethyl-1,3,2-dioxaborolane were added dropwise to the reaction solution, the reaction solution was stirred at 100° C. for 5 hours. After the completion of the reaction, the organic layer of the reaction solution was extracted with ethyl acetate and dried with anhydrous sodium sulfate. After the solvent was evaporated under reduced pressure, the remainder was purified by silica gel column chromatography (developing solvent: hexane/toluene mixed solvent), whereby 1.9 g of a monopinacolfluorene trimer [16] as a white crystal was obtained (60% yield).

(3) The following reagents and solvents were placed in a 200-ml three-necked flask.
Dibromofluorene trimer [10]: 1.0 g (1.04 mmol)
Monopinacol fluorene trimer [16]: 2.2 g (2.23 mmol)
Toluene: 80 ml
Ethanol: 40 ml Next, an aqueous solution prepared by dissolving 2 g of sodium carbonate in 10 ml of water was added dropwise to the reaction solution while the reaction solution was stirred in a nitrogen atmosphere at room temperature. Subsequently, 0.06 g (0.05 mmol) of tetrakis(triphenylphosphine)palladium (0) was added to the reaction solution. Next, after the reaction solution was stirred at room temperature for 30 minutes, the temperature of the reaction solution was increased to 77° C., and then, the reaction solution was stirred for 5 hours. After the completion of the reaction, the organic layer of the reaction solution was extracted with chloroform and dried with anhydrous sodium sulfate. After the solvent was evaporated under reduced pressure, the remainder was purified by silica gel column chromatography (developing solvent: hexane/toluene mixed solvent), whereby 1.8 g of Exemplified Compound No. 9 as a white crystal was obtained (65% yield). The purity of the obtained Exemplified Compound No. 9 was 99.9 wt % and its molecular weight was 2,602.

Example 1

An organic light-emitting device having the structure shown in FIG. 1 was produced. Here, as the constituent materials of the organic light-emitting device, the below-mentioned compounds were used.
Substrate 1: glass substrate
Anode 2: indium tin oxide (ITO)
Hole-injection layer 3: PEDOT:PSS (P AI-4083 (trade name); manufactured by Baytron)
Light-emitting layer 4: Exemplified Compound No. 2 (oligofluorene compound), Exemplified Compound No. 101 (polyfluorene compound (average molecular weight: 76,000 g/mol, manufactured by John Wiley & Sons, Inc.)), and Ir($C_8$-piq)$_3$

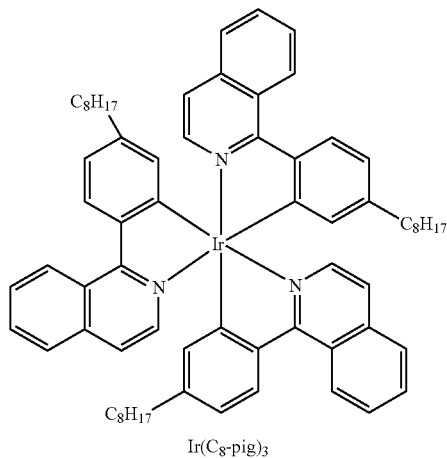

Ir($C_8$-piq)$_3$

Electron injection layer 5: $CsCO_3$
Cathode 6: Al
Specifically, the organic light-emitting device was produced by the following procedure.
First, an ITO was formed into a film on the glass substrate (substrate 1) by a sputtering method to form the anode 2. At this time, the film thickness of the anode 2 was 120 nm. Next, PEDOT:PSS was formed into a film by a spin coating method to form the hole injection layer 3. At this time, the film thickness of the hole injection layer 3 was 30 nm.
Next, a 1.0 wt % toluene solution of Exemplified Compound No. 2, a 1.0 wt % toluene solution of Exemplified Compound No. 101, and a 1.0 wt % toluene solution of Ir($C_8$-piq)$_3$ were prepared. Subsequently, the respective toluene solutions were mixed such that the concentration ratio by weight of the respective solutions was Exemplified Compound No. 2: Exemplified Compound No. 101: Ir($C_8$-piq)$_3$=92:7:1. Then, the mixed solution was formed into a film on the hole injection layer 3 by a spin coating method to form the light-emitting layer 4. At this time, the film thickness of the light-emitting layer 4 was about 90 nm.
Next, $Cs_2CO_3$ was formed into a film on the light-emitting layer 4 by a vacuum evaporation method to form the electron injection layer 5. At this time, the film thickness of the electron injection layer 5 was 2.4 nm. Subsequently, aluminum was formed into a film on the electron injection layer 5 by a vacuum evaporation method to form the cathode 6. At this time, the film thickness of the cathode was 150 nm. Then, the resulting member was covered with a glass plate for protection in a nitrogen atmosphere and encapsulated with an acrylic resin-based adhesive. By the procedure as described above, the organic light-emitting device was obtained.

When the ITO film was connected to a positive electrode of a power source and the Al layer was connected to a negative electrode of the power source and a DC voltage was applied to the obtained organic light-emitting device, red light emission was observed. The red emission had CIE chromaticity coordinates of (X,Y)=(0.65, 0.33). Other characteristics were also evaluated. Incidentally, the respective characteristics were evaluated based on the results of measurement with an organic EL light-emitting characteristic evaluation apparatus (manufactured by CRADLE CORP.). The evaluation apparatus includes a camera obscure, a luminance meter, a multichannel spectroscope, a device driving source, and an analyzer unit. In addition, with the evaluation apparatus, by controlling a driving current and a driving voltage for a device to be evaluated in a programmed manner, a luminance, a current-luminance characteristic, a voltage-luminance characteristic, and a voltage-current characteristic of the device are obtained, whereby the luminance, maximum external quantum efficiency and power efficiency can be measured.
Table 1 shows the evaluation results.

Example 2

An organic light-emitting device was produced by following the same procedure as in Example 1 with the exception that the respective toluene solutions were mixed such that the concentration ratio by weight of the respective toluene solutions was Exemplified Compound No. 2: Exemplified Compound No. 101: Ir($C_8$-piq)$_3$=84:15:1 instead of 92:7:1 in Example 1. When a DC voltage was applied to the thus obtained organic light-emitting device, red light emission was observed as with Example 1. In addition, the organic light-emitting device was evaluated in the same manner as in Example 1. Table 1 shows the results.

Example 3

An organic light-emitting device was produced by following the same procedure as in Example 1 with the exception that the respective toluene solutions were mixed such that the concentration ratio by weight of the respective toluene solutions was Exemplified Compound No. 2: Exemplified Compound No. 101: Ir($C_8$-piq)$_3$=59:40:1 instead of 92:7:1 in Example 1. When a DC voltage was applied to the thus obtained organic light-emitting device, red light emission was observed as with Example 1. In addition, the organic light-emitting device was evaluated in the same manner as in Example 1. Table 1 shows the results.

Comparative Example 1

An organic light-emitting device was produced by following the same procedure as in Example 1 with the exception that Exemplified Compound No. 101 was not used and the toluene solutions of Exemplified Compound No. 2 and Ir($C_8$-piq)$_3$ were mixed such that the concentration ratio by weight of the toluene solutions was Exemplified Compound No. 2: Ir($C_8$-piq)$_3$=99:1. When a DC voltage was applied to the thus obtained organic light-emitting device, red light emission was observed as with Example 1. In addition, the organic light-emitting device was evaluated in the same manner as in Example 1. Table 1 shows the results.

Comparative Example 2

An organic light-emitting device was produced by following the same procedure as in Example 1 with the exception that Exemplified Compound No. 2 was not used and the toluene solutions of Exemplified Compound No. 101 and Ir($C_8$-piq)$_3$ were mixed such that the concentration ratio by weight of the toluene solutions was Exemplified Compound No. 101: Ir($C_8$-piq)$_3$=99:1. When a DC voltage was applied to the thus obtained organic light-emitting device, red light emission was observed as with Example 1. In addition, the organic light-emitting device was evaluated in the same manner as in Example 1. Table 1 shows the results.

Comparative Example 3

A 1 wt % toluene solution was prepared by using Comparative Compound No. 1 (molecular weight: 830; purity: 99.9%) represented below instead of Exemplified Compound No. 2 used in Example 1. In addition, when the light-emitting layer 4 was formed, the respective toluene solutions were mixed such that the concentration ratio by weight of toluene solutions was Comparative Compound No. 1: Exemplified Compound No. 101: Ir($C_8$-piq)$_3$=49:50:1. An organic light-emitting device was produced by following the same procedure as in Example 1, except the forgoing. When a DC voltage was applied to the thus obtained organic light-emitting device, red light emission was observed as with Example 1. In addition, the organic light-emitting device was evaluated in the same manner as in Example 1. Table 1 shows the results.

Example 4

An organic light-emitting device was produced by following the same procedure as in Example 1 with the exception that Ir($C_8$-piq)$_3$ was not used and the toluene solutions of Exemplified Compound Nos. 2 and 101 were mixed such that the concentration ratio by weight of the toluene solutions was Exemplified Compound No. 2: Exemplified Compound No. 101=90:10. When a DC voltage was applied to the thus obtained organic light-emitting device, blue light emission derived from fluorene was observed. The blue emission had CIE chromaticity coordinates of (X,Y)=(0.18, 0.14). In addition, the organic light-emitting device was evaluated in the same manner as in Example 1. Table 2 shows the results.

Example 5

An organic light-emitting device was produced by following the same procedure as in Example 4 with the exception that the concentration ratio by weight of the toluene solutions was Exemplified Compound No. 2: Exemplified Compound No. 101=70:30. When a DC voltage was applied to the thus obtained organic light-emitting device, blue light emission was observed as with Example 4. In addition, the organic light-emitting device was evaluated in the same manner as in Example 4. Table 2 shows the results.

Comparative Example 4

An organic light-emitting device was produced by following the same procedure as in Example 4 with the exception that only a 1 wt % toluene solution of Exemplified Compound No. 2 was used to form the light-emitting layer 4. When a DC voltage was applied to the thus obtained organic light-emit-

TABLE 1

Comparative Compound No. 1

| | Quantity of coating liquid for light-emitting layer formation | | | | | |
|---|---|---|---|---|---|---|
| | Exemplified Compd. No. 2 (wt %) | Exemplified Compd. No. 101 (wt %) | Ir ($C_8$-piq)$_3$ (wt %) | Comp. Compd. No. 1 (wt %) | Maximum external quantum efficiency (%) | Power efficiency (lm/W) | Luminance (cd/m$^2$) |
| Ex. 1 | 92 | 7 | 1 | — | 4.3 | 3.0 | 1,420 |
| Ex. 2 | 84 | 15 | 1 | — | 5.1 | 4.0 | 2,010 |
| Ex. 3 | 59 | 40 | 1 | — | 6.3 | 5.5 | 2,600 |
| Comp. Ex. 1 | 99 | — | 1 | — | 4.3 | 2.4 | 850 |
| Comp. Ex. 2 | — | 99 | 1 | — | 1.2 | 0.3 | 600 |
| Comp. Ex. 3 | — | 50 | 1 | 49 | 3.0 | 1.9 | 800 | ting device, blue light emission was observed as with Example 4. In addition, the organic light-emitting device was evaluated in the same manner as in Example 4. Table 2 shows the results.

Comparative Example 5

An organic light-emitting device was produced by following the same procedure as in Example 4 with the exception that only a 1 wt % toluene solution of Exemplified Compound No. 101 was used to form the light-emitting layer 4. When a DC voltage was applied to the thus obtained organic light-emitting device, blue light emission was observed as with Example 4. In addition, the organic light-emitting device was evaluated in the same manner as in Example 4. Table 2 shows the results.

TABLE 2

| | Quantity of coating liquid for light-emitting layer formation | | Maximum | | |
| --- | --- | --- | --- | --- | --- |
| | Exemplified Compd. No. 2 (wt %) | Exemplified Compd. No. 101 (wt %) | external quantum efficiency (%) | Power efficiency (lm/W) | Luminance (cd/m$^2$) |
| Ex. 4 | 90 | 10 | 1.5 | 1.5 | 1,000 |
| Ex. 5 | 70 | 30 | 2.3 | 2.4 | 1,800 |
| Comp. Ex. 4 | 100 | — | 0.6 | 0.7 | 830 |
| Comp. Ex. 5 | — | 100 | 0.5 | 0.4 | 700 |

Example 6

A 1 wt % toluene solution was prepared by using Exemplified Compound No. 3 instead of Exemplified Compound No. 2 used in Example 1. In addition, when the light-emitting layer 4 was formed, the respective toluene solutions were mixed such that the concentration ratio by weight of the toluene solutions was Exemplified Compound No. 3: Exemplified Compound No. 101: Ir(C$_8$-piq)$_3$=92:7:1. An organic light-emitting device was produced by following the same procedure as in Example 1, except the forgoing. When a DC voltage was applied to the thus obtained organic light-emitting device, red light emission was observed as with Example 1. In addition, the organic light-emitting device was evaluated in the same manner as in Example 1. Table 3 shows the results.

Example 7

An organic light-emitting device was produced by following the same procedure as in Example 6 with the exception that the respective toluene solutions were mixed such that the concentration ratio by weight of the toluene solutions was Exemplified Compound No. 3: Exemplified Compound No. 101: Ir(C$_8$-piq)$_3$=64:35:1. When a DC voltage was applied to the thus obtained organic light-emitting device, red light emission was observed as with Example 6. In addition, the organic light-emitting device was evaluated in the same manner as in Example 6. Table 3 shows the results.

Comparative Example 6

An organic light-emitting device was produced by following the same procedure as in Example 6 with the exception that Exemplified Compound No. 101 was not used and the toluene solutions of Exemplified Compound No. 3 and Ir(C$_8$-piq)$_3$ were mixed such that the concentration ratio by weight of the toluene solutions was Exemplified Compound No. 3: Ir(C$_8$-piq)$_3$=99:1. When a DC voltage was applied to the thus obtained organic light-emitting device, red light emission was observed as with Example 6. In addition, the organic light-emitting device was evaluated in the same manner as in Example 6. Table 3 shows the results.

TABLE 3

| | Quantity of coating liquid for light-emitting layer formation | | | Maximum | | |
| --- | --- | --- | --- | --- | --- | --- |
| | Exemplified Compd. No. 3 (wt %) | Exemplified Compd. No. 101 (wt %) | Ir(C$_8$-piq)$_3$ (wt %) | external quantum efficiency (%) | Power efficiency (lm/W) | Luminance (cd/m$^2$) |
| Ex. 6 | 92 | 7 | 1 | 4.9 | 3.8 | 1,980 |
| Ex. 7 | 64 | 35 | 1 | 6.7 | 6.0 | 2,900 |
| Comp. Ex. 6 | 99 | — | 1 | 4.5 | 2.9 | 990 |

Example 8

A 1 wt % toluene solution was prepared by using Exemplified Compound No. 12 instead of Exemplified Compound No. 2 used in Example 1. In addition, when the light-emitting layer 4 was formed, the respective toluene solutions were mixed such that the concentration ratio by weight of the toluene solutions was Exemplified Compound No. 12: Exemplified Compound No. 101: Ir(C$_8$-piq)$_3$=85:10:5. An organic light-emitting device was produced by following the same procedure as in Example 1, except the forgoing. When a DC voltage was applied to the thus obtained organic light-emitting device, red light emission was observed as with Example 1. In addition, the organic light-emitting device was evaluated in the same manner as in Example 1. Table 4 shows the results.

Example 9

An organic light-emitting device was produced by following the same procedure as in Example 8 with the exception that the respective toluene solutions were mixed such that the concentration ratio by weight of the toluene solutions was Exemplified Compound No. 12: Exemplified Compound No. 101: Ir($C_8$-piq)$_3$=60:35:5. When a DC voltage was applied to the thus obtained organic light-emitting device, red light emission was observed as with Example 8. In addition, the organic light-emitting device was evaluated in the same manner as in Example 8. Table 4 shows the results.

Comparative Example 7

An organic light-emitting device was produced by following the same procedure as in Example 8 with the exception that Exemplified Compound No. 101 was not used and the toluene solutions of Exemplified Compound No. 12 and Ir($C_8$-piq)$_3$ were mixed such that the concentration ratio by weight of toluene solutions was Exemplified Compound No. 12: Ir($C_8$-piq)$_3$=95:5. When a DC voltage was applied to the thus obtained organic light-emitting device, red light emission was observed as in Example 8. In addition, the organic light-emitting device was evaluated in the same manner as in Example 8. Table 4 shows the results.

of 2,772. In addition, when the light-emitting layer 4 was formed, the respective toluene solutions were mixed such that the concentration ratio by weight of toluene solutions was Exemplified Compound No. 13: Exemplified Compound No. 101: Ir($C_8$-piq)$_3$=80:19:1. An organic light-emitting device was produced by following the same procedure as in Example 1, except the forgoing. When a DC voltage was applied to the thus obtained organic light-emitting device, red light emission was observed as with Example 1. In addition, the organic light-emitting device was evaluated in the same manner as in Example 1. Table 5 shows the results.

Example 11

An organic light-emitting device was produced by following the same procedure as in Example 10 with the exception that the respective toluene solutions were mixed such that the concentration ratio by weight of toluene solutions was Exemplified Compound No. 13: Exemplified Compound No. 101: Ir($C_8$-piq)$_3$=65:34:1. When a DC voltage was applied to the thus obtained organic light-emitting device, red light emission was observed as with Example 10. In addition, the organic light-emitting device was evaluated in the same manner as in Example 10. Table 5 shows the results.

Comparative Example 8

An organic light-emitting device was produced by following the same procedure as in Example 10 with the exception

TABLE 4

| | Quantity of coating liquid for light-emitting layer formation | | | Maximum | | |
|---|---|---|---|---|---|---|
| | Exemplified Compd. No. 12 (wt %) | Exemplified Compd. No. 101 (wt %) | Ir($C_8$-piq)$_3$ (wt %) | external quantum efficiency (%) | Power efficiency (lm/W) | Luminance (cd/m$^2$) |
| Ex. 8 | 85 | 10 | 5 | 5.1 | 4.1 | 2,020 |
| Ex. 9 | 60 | 35 | 5 | 6.3 | 6.3 | 3,000 |
| Comp. Ex. 7 | 95 | — | 5 | 3.8 | 3.0 | 1,050 |

Example 10

A 1 wt % toluene solution was prepared by using Exemplified Compound No. 13 instead of Exemplified Compound No. 2 used in Example 1. Incidentally, Exemplified Compound No. 13 was a compound synthesized by referring to J. Am. CHEM. SOC., A. L. Kanibolotsky et al., 2004, 126, p 13695 and had a purity of 99.7 wt % and a molecular weight that Exemplified Compound No. 101 was not used and the toluene solutions of Exemplified Compound No. 13 and Ir($C_8$-piq)$_3$ were mixed such that the concentration ratio by weight of toluene solutions was Exemplified Compound No. 13: Ir($C_8$-piq)$_3$=99:1. When a DC voltage was applied to the thus obtained organic light-emitting device, red light emission was observed as with Example 10. In addition, the organic light-emitting device was evaluated in the same manner as in Example 10. Table 5 shows the results.

TABLE 5

| | Quantity of coating liquid for light-emitting layer formation | | | Maximum external quantum efficiency (%) | Power efficiency (lm/W) | Luminance (cd/m$^2$) |
|---|---|---|---|---|---|---|
| | Exemplified Compd. No. 13 (wt %) | Exemplified Compd. No. 101 (wt %) | Ir(C$_8$-piq)$_3$ (wt %) | | | |
| Ex. 10 | 80 | 19 | 1 | 5.2 | 3.8 | 2,010 |
| Ex. 11 | 65 | 34 | 1 | 6.3 | 6.0 | 2,930 |
| Comp. Ex. 8 | 99 | — | 1 | 4.0 | 3.1 | 1,020 |

Example 12

1 wt % toluene solutions were prepared, respectively, by using Exemplified Compound No. 15 instead of Exemplified Compound No. 2 used in Example 1 and by using Exemplified Compound No. 109 (average molecular weight: 1,100,000 g/mol; manufactured by SIGMA-ALDRICH CORP.) instead of Exemplified Compound No. 101 used in Example 1. Incidentally, Exemplified Compound No. 15 was a material synthesized by referring to Tetrahedron. Lett., G. L. Feng et al., 2006, 47, p 7089 and had a purity of 99.6 wt % and a molecular weight of 2,092. In addition, when the light-emitting layer 4 was formed, the respective toluene solutions were mixed such that the concentration ratio by weight of toluene solutions was Exemplified Compound No. 15: Exemplified Compound No. 109: Ir(C$_8$-piq)$_3$=75:20:5. An organic light-emitting device was produced by following the same procedure as in Example 1, except the forgoing. When a DC voltage was applied to the thus obtained organic light-emitting device, red light emission was observed as with Example 1. In addition, the organic light-emitting device was evaluated in the same manner as in Example 1. Table 6 shows the results.

Example 13

An organic light-emitting device was produced by following the same procedure as in Example 12 with the exception that the respective toluene solutions were mixed such that the concentration ratio by weight of the toluene solutions was Exemplified Compound No. 15: Exemplified Compound No. 109: Ir(C$_8$-piq)$_3$=60:35:5. When a DC voltage was applied to the thus obtained organic light-emitting device, red light emission was observed as with Example 12. In addition, the organic light-emitting device was evaluated in the same manner as in Example 12. Table 6 shows the results.

Comparative Example 9

An organic light-emitting device was produced by following the same procedure as in Example 12 with the exception that Exemplified Compound No. 109 was not used and the toluene solutions of Exemplified Compound No. 15 and Ir(C$_8$-piq)$_3$ were mixed such that the concentration ratio by weight of the toluene solutions was Exemplified Compound No. 15: Ir(C$_8$-piq)$_3$=95:5. When a DC voltage was applied to the thus obtained organic light-emitting device, red light emission was observed as with Example 12. In addition, the organic light-emitting device was evaluated in the same manner as in Example 12. Table 6 shows the results.

Comparative Example 10

An organic light-emitting device was produced by following the same procedure as in Example 12 with the exception that Exemplified Compound No. 15 was not used and the toluene solutions of Exemplified Compound No. 109 and Ir(C$_8$-piq)$_3$ were mixed such that the concentration ratio by weight of the toluene solutions was Exemplified Compound No. 109: Ir(C$_8$-piq)$_3$=95:5. When a DC voltage was applied to the thus obtained organic light-emitting device, red light emission was observed as with Example 12. In addition, the organic light-emitting device was evaluated in the same manner as in Example 12. Table 6 shows the results.

TABLE 6

| | Quantity of coating liquid for light-emitting layer formation | | | Maximum external quantum efficiency (%) | Power efficiency (lm/W) | Luminance (cd/m$^2$) |
|---|---|---|---|---|---|---|
| | Exemplified Compd. No. 15 (wt %) | Exemplified Compd. No. 109 (wt %) | Ir(C$_8$-piq)$_3$ (wt %) | | | |
| Ex. 12 | 75 | 20 | 5 | 1.5 | 1.3 | 800 |
| Ex. 13 | 60 | 35 | 5 | 2.0 | 1.9 | 920 |
| Comp. Ex. 9 | 95 | — | 5 | 0.7 | 0.7 | 530 |
| Comp. Ex. 10 | — | 95 | 5 | 0.2 | 0.2 | 210 |

Example 14

1 wt % toluene solutions were prepared, respectively, by using Exemplified Compound No. 9 instead of Exemplified Compound No. 2 used in Example and by using Exemplified Compound No. 104 (average molecular weight: 100,000 g/mol; manufactured by John Wiley & Sons, Inc.) instead of Exemplified Compound NO. 101 used in Example 1. In addition, when the light-emitting layer 4 was formed, the respective solutions were mixed such that the concentration ratio by weight of the toluene solutions was Exemplified Compound No. 9: Exemplified Compound No. 104: Ir(C$_8$-piq)$_3$=85:5:10 An organic light-emitting device was produced by following the same procedure as in Example 1, except the forgoing. When a DC voltage was applied to the thus obtained organic light-emitting device, red light emission was observed as with Example 1.

In addition, the organic light-emitting device was evaluated for the half lifetime when an initial luminance was set to 100 cd/m$^2$. For the measurement of the half lifetime, the same apparatus as used for measuring the maximum external quantum efficiency, the power efficiency, and the luminance described above. Incidentally, the term "half lifetime" refers to the time it takes for the initial luminance of 100 cd/m$^2$ to decrease to its half value. Table 7 shows the results.

Example 15

An organic light-emitting device was produced by following the same procedure as in Example 14 with the exception that the respective toluene solutions were mixed such that the concentration ratio by weight of the toluene solutions was Exemplified Compound No. 9: Exemplified Compound No. 104: Ir(C$_8$-piq)$_3$=80:10:10. When a DC voltage was applied to the thus obtained organic light-emitting device, red light emission was observed as with Example 14. In addition, the organic light-emitting device was evaluated in the same manner as in Example 14. Table 7 shows the results.

Example 16

An organic light-emitting device was produced by following the same procedure as in Example 14 with the exception that the respective toluene solutions were mixed such that the concentration ratio by weight of the toluene solutions was Exemplified Compound No. 9: Exemplified Compound No. 104: Ir(C$_8$-piq)$_3$=70:20:10. When a DC voltage was applied to the thus obtained organic light-emitting device, red light emission was observed as with Example 14. In addition, the organic light-emitting device was evaluated in the same manner as in Example 14. Table 7 shows the results.

Example 17

An organic light-emitting device was produced by following the same procedure as in Example 14 with the exception that the respective toluene solutions were mixed such that the concentration ratio by weight of the toluene solutions was Exemplified Compound No. 9: Exemplified Compound No. 104: Ir(C$_8$-piq)$_3$=60:30:10. When a DC voltage was applied to the thus obtained organic light-emitting device, red light emission was observed as with Example 14. In addition, the organic light-emitting device was evaluated in the same manner as in Example 14. Table 7 shows the results.

Comparative Example 11

An organic light-emitting device was produced by following the same procedure as in Example 14 with the exception that Exemplified Compound No. 104 was not used and the toluene solutions of Exemplified Compound No. 9 and Ir(C$_8$-piq)$_3$ were mixed such that the concentration ratio by weight of the toluene solutions was Exemplified Compound No. 9: Ir(C$_8$-piq)$_3$=90:10. When a DC voltage was applied to the thus obtained organic light-emitting device, red light emission was observed as with Example 14. In addition, the organic light-emitting device was evaluated in the same manner as in Example 14. Table 7 shows the results.

Comparative Example 12

An organic light-emitting device was produced by following the same procedure as in Example 14 with the exception that Exemplified Compound No. 9 was not used and the toluene solutions of Exemplified Compound No. 104 and Ir(C$_8$-piq)$_3$ were mixed such that the concentration ratio by weight of the toluene solutions was Exemplified Compound No. 104: Ir(C$_8$-piq)$_3$=90:10. When a DC voltage was applied to the thus obtained organic light-emitting device, red light emission was observed as with Example 14. In addition, the organic light-emitting device was evaluated in the same manner as in Example 14. Table 7 shows the results.

Comparative Example 13

A 1 wt % toluene solution was prepared by using Comparative Compound No. 1 instead of Exemplified Compound No. 9 used in Example 14. In addition, when the light-emitting layer 4 was formed, the respective solutions were mixed such that the concentration ratio by weight of the toluene solutions was Comparative Compound No. 1: Exemplified Compound No. 104: Ir(C$_8$-piq)$_3$=45:45:10. An organic light-emitting device was produced by following the same procedure as in Example 14, except the forgoing. When a DC voltage was applied to the thus obtained organic light-emitting device, red light emission was observed as with Example 14. In addition, the organic light-emitting device was evaluated in the same manner as in Example 14. Table 7 shows the results.

TABLE 7

| | Quantity of coating liquid for light-emitting layer formation | | | | |
| --- | --- | --- | --- | --- | --- |
| | Exemplified Compd. No. 9 (wt %) | Exemplified Compd. No. 104 (wt %) | Ir(C$_8$-piq)$_3$ (wt %) | Comp. Compd. No. 1 (wt %) | Half lifetime @100 cd/m$^2$ (hour) |
| Ex. 14 | 85 | 5 | 10 | — | 1,500 |
| Ex. 15 | 80 | 10 | 10 | — | 2,200 |
| Ex. 16 | 70 | 20 | 10 | — | 2,500 |
| Ex. 17 | 60 | 30 | 10 | — | 3,500 |
| Comp. Ex. 11 | 90 | — | 10 | — | 100 |
| Comp. Ex. 12 | — | 90 | 10 | — | 200 |
| Comp. Ex. 13 | — | 45 | 10 | 45 | 500 |

Example 18

A 1 wt % toluene solution was prepared by using Exemplified Compound No. 12 instead of Exemplified Compound No. 9 used in Example 14. In addition, when the light-emitting layer 4 was formed, the respective solutions were mixed such that the concentration ratio by weight of the toluene solutions was Exemplified Compound No. 12: Exemplified Compound No. 104: Ir(C$_8$-piq)$_3$=75:15:10. An organic light-emitting device was produced by following the same procedure as in Example 14, except the forgoing. When a DC voltage was applied to the thus obtained organic light-emitting device, red light emission was observed as with Example 14. In addition, the organic light-emitting device was evaluated in the same manner as in Example 14. Table 8 shows the results.

Example 19

An organic light-emitting device was produced by following the same procedure as in Example 18 with the exception that the respective solutions were mixed such that the concentration ratio by weight of the toluene solutions was Exemplified Compound No. 12: Exemplified Compound No. 104: $Ir(C_8\text{-piq})_3=65:25:10$. When a DC voltage was applied to the thus obtained organic light-emitting device, red light emission was observed as with Example 18. In addition, the organic light-emitting device was evaluated in the same manner as in Example 18. Table 8 shows the results.

Example 20

An organic light-emitting device was produced by following the same procedure as in Example 18 with the exception that the respective solutions were mixed such that the concentration ratio by weight of the toluene solutions was Exemplified Compound No. 12: Exemplified Compound No. 104: $Ir(C_8\text{-piq})_3=55:35:10$. When a DC voltage was applied to the thus obtained organic light-emitting device, red light emission was observed as with Example 18. In addition, the organic light-emitting device was evaluated in the same manner as in Example 18. Table 8 shows the results.

Comparative Example 14

An organic light-emitting device was produced by following the same procedure as in Example 18 with the exception that Exemplified Compound No. 104 was not used and the toluene solutions of Exemplified Compound No. 12 and $Ir(C_8\text{-piq})_3$ were mixed such that the concentration ratio by weight of the toluene solutions was Exemplified Compound No. 12: $Ir(C_8\text{-piq})_3=90:10$. When a DC voltage was applied to the thus obtained organic light-emitting device, red light emission was observed as with Example 18. In addition, the organic light-emitting device was evaluated in the same manner as in Example 18. Table 8 shows the results.

Comparative Example 15

A 1 wt % toluene solution was prepared by using Comparative Compound No. 1 instead of Exemplified Compound No. 12 used in Example 18. In addition, when the light-emitting layer 4 was formed, the respective toluene solutions were mixed such that the concentration ratio by weight of the toluene solutions was Comparative Compound No. 1: Exemplified Compound No. 104: $Ir(C_8\text{-piq})_3=45:45:10$. An organic light-emitting device was produced by following the same procedure as in Example 18, except the forgoing. When a DC voltage was applied to the thus obtained organic light-emitting device, red light emission was observed as with Example 18. In addition, the organic light-emitting device was evaluated in the same manner as in Example 18. Table 8 shows the results.

TABLE 8

| | Quantity of coating liquid for light-emitting layer formation | | | | Half lifetime @100 cd/m² (hour) |
|---|---|---|---|---|---|
| | Exemplified Compd. No. 12 (wt %) | Exemplified Compd. No. 104 (wt %) | $Ir(C_8\text{-piq})_3$ (wt %) | Comp. Compd. No. 1 (wt %) | |
| Ex. 18 | 75 | 15 | 10 | — | 1,800 |
| Ex. 19 | 65 | 25 | 10 | — | 2,100 |
| Ex. 20 | 55 | 35 | 10 | — | 2,300 |
| Comp. Ex. 14 | 90 | — | 10 | — | 20 |
| Comp. Ex. 15 | — | 45 | 10 | 45 | 400 |

As shown in Tables 1 to 8, the organic light-emitting device of the present invention in which the light-emitting layer 4 includes an oligomer material and a polymer material in combination can realize a device which has a higher efficiency and is driven at a lower voltage than an organic light-emitting device in which a light-emitting layer includes only an oligomer material or only a polymer material.

Figure 7A:
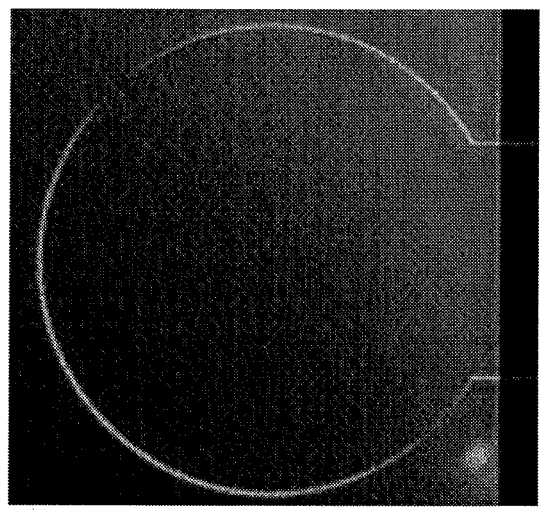
FIGS. 7A and 7B are optical microscope photographs of a light-emitting layer.
Figure 7B:
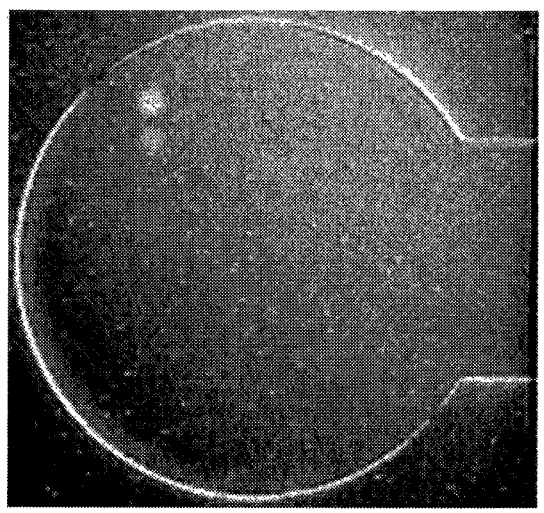

FIGS. 7A and 7B are optical microscope photographs of light-emitting layers, and FIG. 7A is a photograph in the case of Example 1 and FIG. 7B is a photograph in the case of Comparative Example 3. When the light-emitting layer 4 was formed using Comparative Compound No. 1 instead of an oligomer material, it was confirmed that Comparative Compound No. 1 was crystallized and deposited as shown in FIG. 7B. On the other hand, in the light-emitting devices of Example 1, such crystallization was not observed as shown in FIG. 7A. The reason for this is considered to be that the molecular weight of the oligomer material used in Example 1 is larger than that of Comparative Compound No. 1, whereby a film having higher amorphous property can be formed.

Figure 8A:
FIGS. 8A and 8B are scanning electron microscope photographs of a light-emitting layer surface.
Figure 8B:
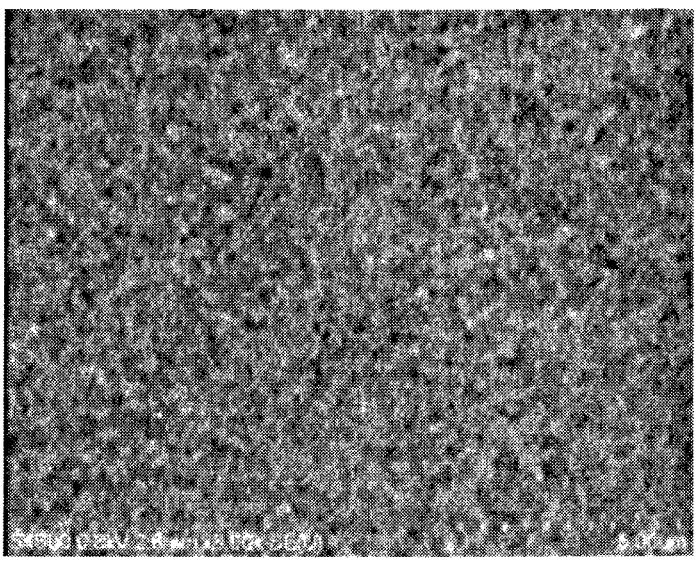
Figure 9:
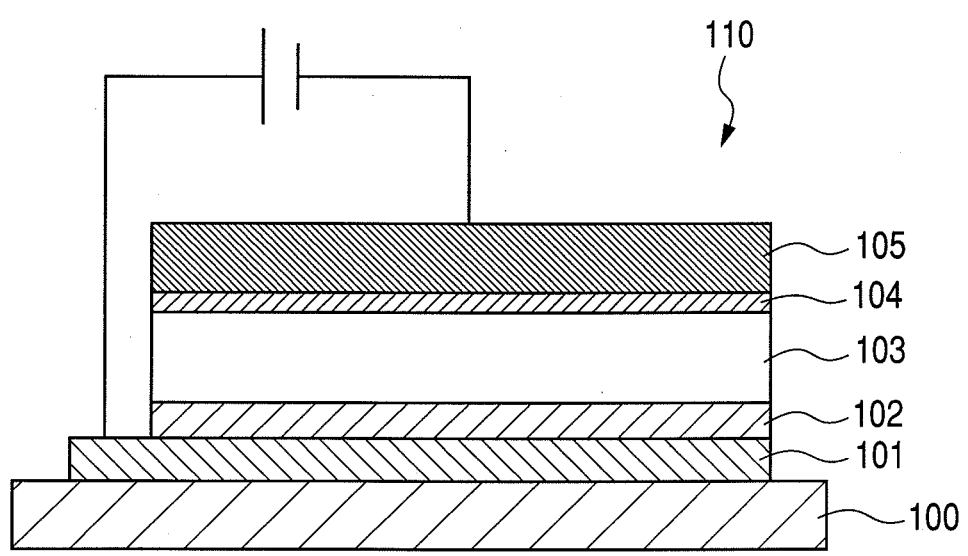
FIG. 9 is a cross-sectional view illustrating a general structure of a coating organic light-emitting device.

FIGS. 8A and 8B are scanning electron microscope photographs of light-emitting layer surfaces, and FIG. 8A is a photograph in the case of Example 1 and FIG. 8B is a photograph in the case of Comparative Example 1. It can be seen from the scanning electron microscope photographs that the surface of the light-emitting layer in Comparative Example 1 is rougher than that of Example 1. In addition, in Comparative Example 1, scattering of light due to the surface roughness was confirmed.

The surface roughness of the film observed in Comparative Example 1 is considered to be attributable to that when a thin film serving as a light-emitting layer was formed by solidification, nuclei were formed nonuniformly and Exemplified Compound No. 2 as an oligofluorene compound was diffused and aggregated to the nuclei to thereby form an aggregate. On the other hand, in Example 1, there was observed no such phenomenon and a good amorphous film could be obtained. The reason for this is considered to be that the viscosity of the coating solution was increased by mixing Exemplified Compound No. 101 as a polymer material to reduce the aggregation rate of the oligofluorene compound.

In the organic light-emitting device of the present invention, it has been confirmed that by mixing the oligomer material and the polymer material and forming a light-emitting layer of the mixture, the efficiency of the device can be improved and the driving voltage can be reduced. The reason for this is considered to be that by mixing the oligomer material and the polymer material, the crystallization and aggregation of the oligomer material can be suppressed to improve the film quality, whereby the leak current is reduced and an interface of the light-emitting layer with the hole injection layer or the electron injection layer is uniformly formed to lower an injection barrier.

Further, as shown in Tables 7 and 8, the lifetime of the organic light-emitting device of the present invention was improved by using Exemplified Compound No. 104 which is a polymer material. The reason for this is considered to be that because Exemplified Compound No. 104 is a polymer having an amine skeleton and the HOMO level is increased, the injectability of holes from PEDOT:PSS is improved, with the result that electric charge accumulated at a PEDOT:PSS interface can be reduced.

The organic light-emitting device of the present invention can be produced by a coating process which is an easy and relatively low cost process and can be utilized as a constituent device for a display panel, a display apparatus, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-240660, filed Sep. 18, 2007, which is hereby incorporated by reference in its entirety.

The invention claimed is:

1. An organic light-emitting device comprising:
an anode;
a cathode; and
a light-emitting layer interposed between the anode and the cathode,
wherein the light-emitting layer comprises an oligomer material comprising a plurality of fluorene units and having a single molecular weight ranging from 1,000 to 10,000, a polymer material having a molecular weight distribution, and a triplet light-emitting material, the concentration of the oligomer material being higher than the concentration of the polymer material.

2. A display apparatus, comprising the organic light-emitting device set forth in claim 1.

3. The organic light-emitting device according to claim 1, wherein the polymer material has a molecular weight of 10,000 or more.

4. The organic light-emitting device according to claim 3, wherein the polymer comprises a plurality of fluorene units.

5. The organic light-emitting device according to claim 1, wherein the oligomer material is represented by the following structural formula:

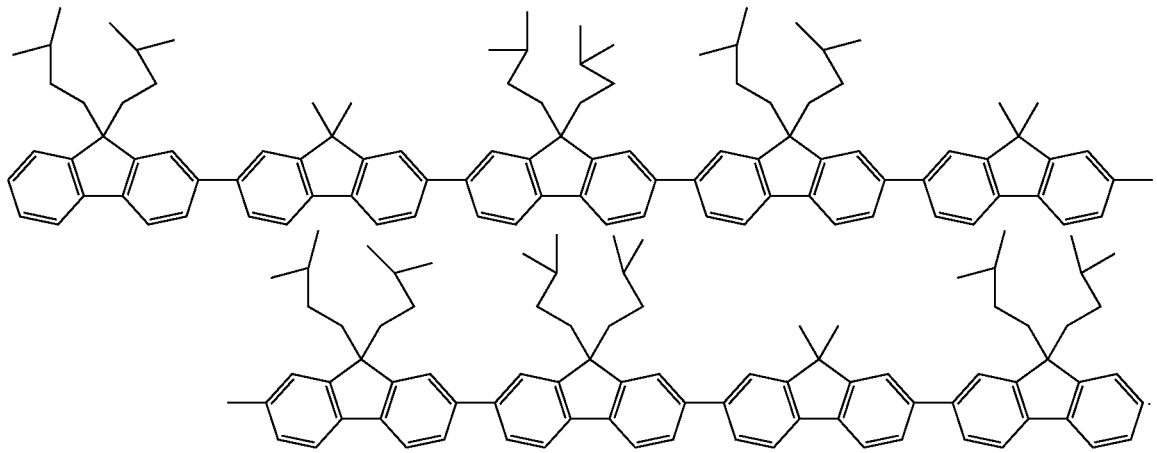

6. The organic light-emitting device according to claim 1, wherein the oligomer material is represented by the following structural formula:

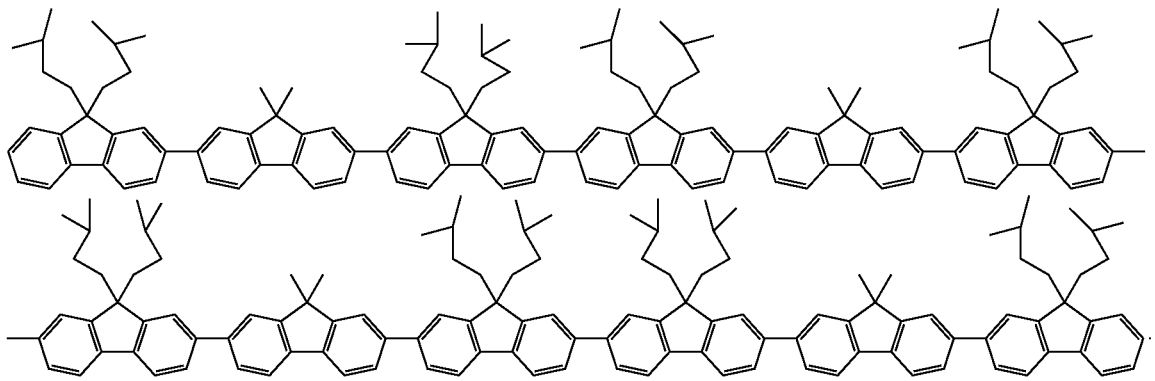

7. The organic light-emitting device according to claim 1, wherein the oligomer material is represented by the following structural formula:
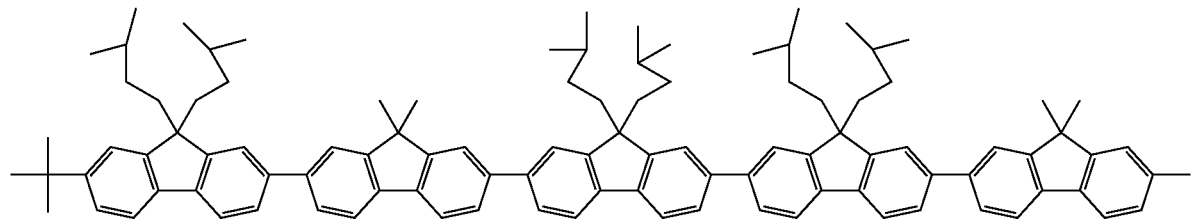
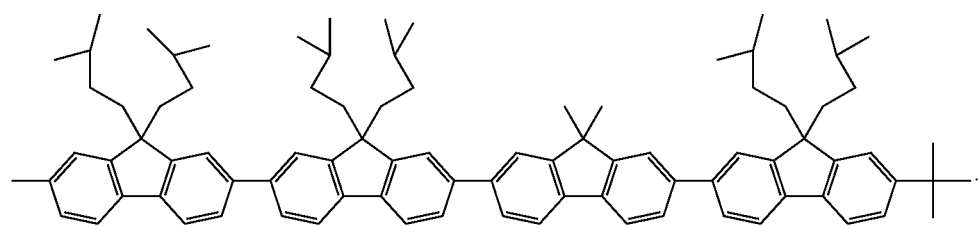
8. The organic light-emitting device according to claim 1, wherein the oligomer material is represented by the following structural formula:
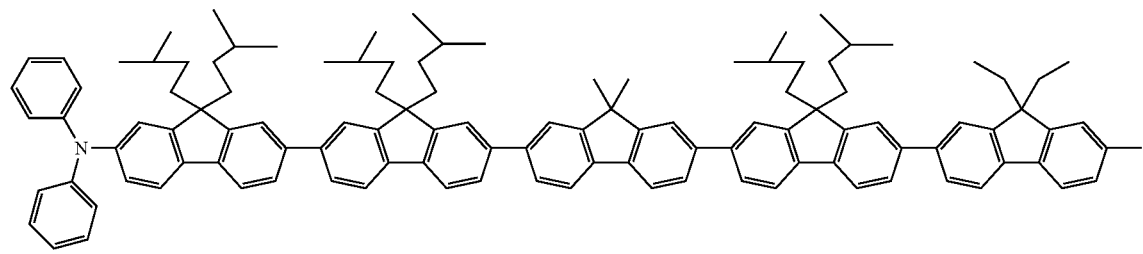
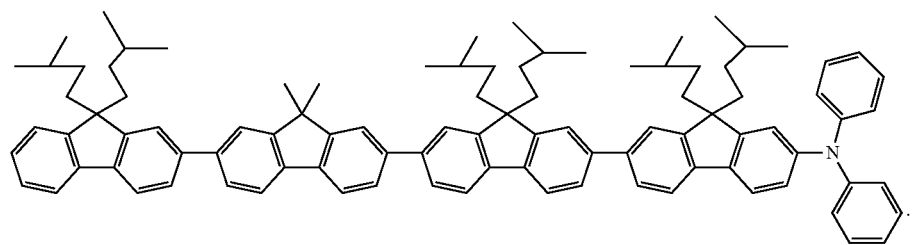

9. The organic light-emitting device according to claim 1, wherein the oligomer material is represented by the following structural formula:

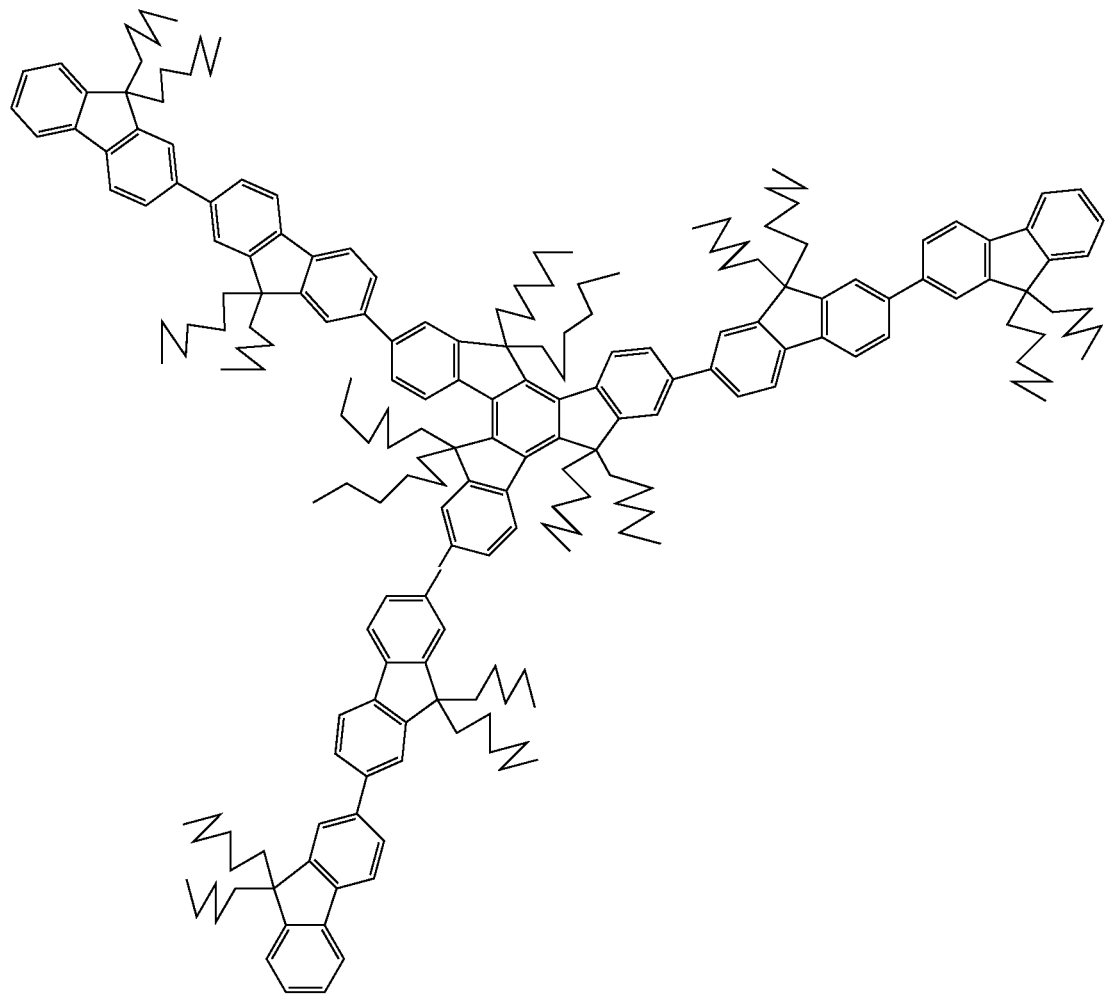

10. An image forming apparatus comprising a photosensitive drum and the organic light-emitting device according to claim 1 for conducting light exposure to the photosensitive drum.

11. An apparatus comprising the organic light-emitting device according to claim 1 and a film for controlling an emission color.

12. An illumination apparatus comprising the organic light-emitting device according to claim 1.

* * * * *